(12) United States Patent
     Mitra

(10) Patent No.: US 10,446,260 B2
(45) Date of Patent: Oct. 15, 2019

(54) SPATIALLY INDEXED TISSUE BIOBANK WITH MICROSCOPIC PHENOTYPE-BASED RETRIEVAL SYSTEM

(71) Applicant: Partha P. Mitra, New York City, NY (US)

(72) Inventor: Partha P. Mitra, New York City, NY (US)

(73) Assignee: Clarapath, Inc., New York City, NY (US)

(*) Notice: Subject to any disclaimer, the term of this patent is extended or adjusted under 35 U.S.C. 154(b) by 89 days.

(21) Appl. No.: 15/130,703

(22) Filed: Apr. 15, 2016

(65) Prior Publication Data

US 2017/0160535 A1    Jun. 8, 2017

Related U.S. Application Data

(60) Provisional application No. 62/264,198, filed on Dec. 7, 2015.

(51) Int. Cl.
*G01N 1/28* (2006.01)
*G16B 20/00* (2019.01)
(Continued)

(52) U.S. Cl.
CPC .............. *G16B 20/00* (2019.02); *G01N 1/06* (2013.01); *G01N 1/286* (2013.01); *G01N 1/36* (2013.01); *C12Q 1/6806* (2013.01); *C12Q 1/6869* (2013.01); *G01N 2001/2873* (2013.01); *G02B 21/34* (2013.01); *G02B 21/367* (2013.01)

(58) Field of Classification Search
CPC ................... G06F 19/18; G01N 1/286; G01N 2001/2886; G01N 1/36; G01N 1/06; G01N 2001/362; G01N 2001/2873; G02B 21/34; G02B 21/367; C12Q 1/6806
USPC .............. 73/863, 863.01, 864.41; 435/287.3, 435/288.3; 422/68.1, 82.05–82.11, 536
See application file for complete search history.

(56) References Cited

U.S. PATENT DOCUMENTS

| | | | | |
|---|---|---|---|---|
| 5,746,855 A | * | 5/1998 | Bolles | B65B 15/04 156/267 |
| 2003/0215936 A1 | * | 11/2003 | Kallioniemi | G01N 1/36 435/287.1 |

(Continued)

*Primary Examiner* — Robert R Raevis
(74) *Attorney, Agent, or Firm* — Leslie Meyer-Leon; IP Legal Strategies Group P.C.

(57) ABSTRACT

The invention is directed to a preserved serial set of sequential, iterative, and ordered thin sections of a specimen block, and a catalog of images taken from one or more sub-series of the set of sections and organized so as to create a three-dimensional profile of the microscopic structures of the specimen block. The serial set of sequential, iterative, and ordered thin sections are prepared from the specimen block by cutting and imaging thin sections of that specimen block so that the thin sections remain strictly in the sequential, iterative, order in which they are cut from the specimen block. A spatial index is created from the cataloged three-dimensional images which is searchable by local content-based image retrieval (LCBIR). The LCBIR query is used to locate, within the three-dimensional index, microscopic structural features, thereby making that portion of the specimen available for further analysis and/or for extraction.

12 Claims, 11 Drawing Sheets

(51) Int. Cl.
   *G01N 1/36*   (2006.01)
   *G01N 1/06*   (2006.01)
   *C12Q 1/6869*   (2018.01)
   *G02B 21/34*   (2006.01)
   *G02B 21/36*   (2006.01)
   *C12Q 1/6806*   (2018.01)

(56) References Cited

U.S. PATENT DOCUMENTS

| | | | |
|---|---|---|---|
| 2003/0236586 A1* | 12/2003 | Tomimatsu | G05B 23/0264 700/110 |
| 2010/0093023 A1* | 4/2010 | Gustafsson | G01N 1/286 435/40.52 |
| 2016/0131559 A1* | 5/2016 | Wimberger-Friedl | G01N 1/286 435/6.12 |

* cited by examiner

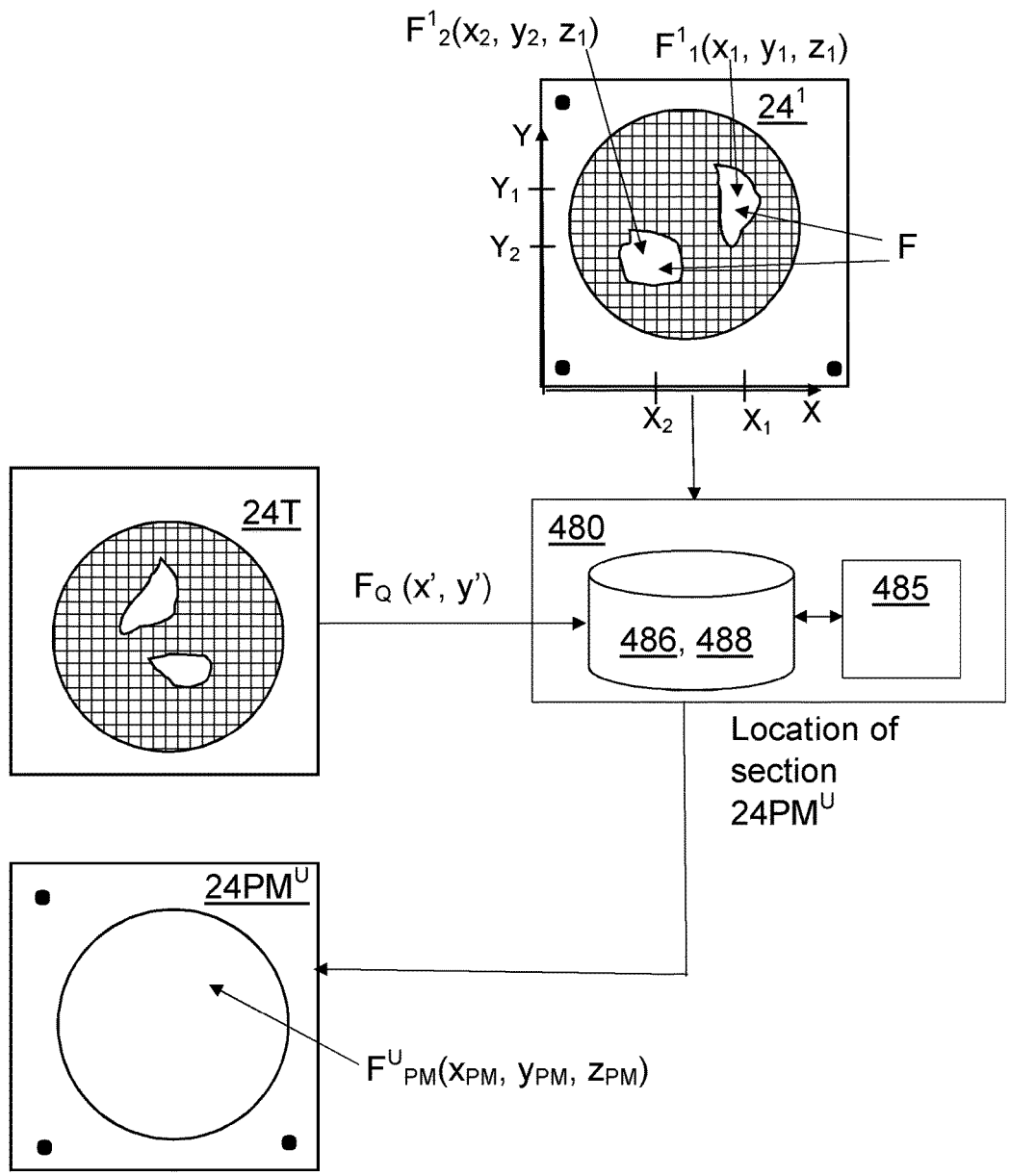

SPATIALLY INDEXED TISSUE BIOBANK WITH MICROSCOPIC PHENOTYPE-BASED RETRIEVAL SYSTEM

FIELD OF THE INVENTION

The invention is in the field of specimen analysis by histochemistry and digital imaging techniques.

BACKGROUND

Human tissue samples obtained during surgical procedures or autopsies are stored for use in future research studies, together with associated metadata. The stored tissue samples are frequently subjected to molecular studies, such as genome or transcriptome analysis. Thus far, standard practice has been to preserve the tissue sample and then store it as a block of tissue, in a storage facility loosely referred to as a "biobank". If a researcher or clinician later wished to examine a particular phenotypic or genotypic feature within a tissue block, the whole block of tissue would have to be retrieved from storage, and the tissue sectioned to obtain the region of the tissue block of interest. In many cases this region is only a small portion of the tissue in the block, so the remainder of the tissue is wasted. Another modality in the practice of anatomic pathology is to cut a tissue block into sections in order to perform histochemical analysis prior to storage in the tissue depository. Each tissue section is placed on a glass slide. Some slides are analyzed with histochemical stains, but other slides, referred to as "blank slides," are stored unstained. In order to retrieve a region of tissue of interest, it has heretofore been necessary to retrieve a blank slide and slightly stain and visualize a section of the stored tissue to determine where the region, or "boundary," may lie. Unfortunately, staining can degrade the very molecule that would have yielded valuable information. Further, this procedure is wasteful, because tissue stored in a block must first be sectioned and some sections discarded.

Thus, it would be an advantage to have a system which stores, and is able to retrieve, a small defined microscopic region of a specimen from a specific physical location within a three-dimensional specimen block, based on known specific micro-structural phenotypic information.

SUMMARY

The systems and processes for phenotype-based retrieval of a portion of a sample disclosed herein can be employed using a tape transfer cryostat-microtome technique for generating a plurality of series of sections of the tissue sample. In a series of tissue sections, at least one of the series may remain unprocessed for later use as a "blank." The blanks, which can be either transferred to slides or retained on the tape, can be transferred to a tissue repository and stored for later analysis by, e.g., genomic, protein, or histological analysis. The remaining sections can be transferred to slides for histochemistry.

Use of a tape transfer technique, either manual tape transfer or the automated tape transfer system disclosed in U.S. Patent Application Ser. No. 62/187,114, filed Jun. 30, 2015, which is hereby incorporated by reference, results in sections that are relatively non-distorted. The relative lack of distortion enables alignment of the two-dimensional x-y coordinates of contiguous sections. In addition, tracking the order of the sections as they are created allows for the sections to be uniquely identified and ordered relative to each other so that three-dimensional data stacking is made possible, thereby, along with un-distorted sections, permitting three-dimensional spatial referencing of the sample (such as the brain) from which the sample was collected.

As disclosed herein, spatial localization within the sections can be achieved by applying spatial reference markings, a.k.a., fiducial marks, to the specimen block from which the sections will be cut so that absolute x-y coordinates can be obtained within each section. Spatial localization enables two-dimensional mapping of the sections using the fiducial elements disclosed above to develop a uniform coordinate system across the section, thus allowing precise identification of features on sections.

The sections targeted for analysis can be stained with histochemical stains, digitally imaged, and subjected to image processing or other data analytics in order to identify and catalog phenotypes for the sample. This spatial index will permit query and retrieval of appropriate sections of tissue, or precise spatial locations within such sections, from which material can be extracted for further histochemical, immunohistochemical, or DNA or RNA analysis.

The spatial index can include the cataloged phenotype and its location on the subject section on which it was identified. Due to the pre-established ordering of the sections, absolute x-y-z coordinates can be obtained among the sections. Therefore, a pointer to a location on a stored, un-analyzed, un-processed section where the cataloged phenotype is likely to occur, should the unprocessed section be histochemically stained, digitally imaged, and analyzed, can be developed and included in the spatial index.

Spatial indexing permits query and retrieval of appropriate unprocessed sections of tissue, or accurate spatial locations within such unprocessed sections, that are associated with features identified in analyzed sections. From the appropriate unprocessed sections of tissue, or accurate spatial locations within such unprocessed sections, so retrieved, material can be extracted for further histochemical, immunohistochemical, or DNA/RNA analysis.

The invention is particularly useful in the field of clinical anatomic pathology, where the purpose of retrieving tissue is to obtain further molecular information about the same patient from whom the stored samples were derived, presumably for the diagnostic or therapeutic benefit of that patient. The invention can also be useful in comparing a second tissue sample obtained from a patient to a first sample collected from the same patient at an earlier date.

The invention has additional advantages for other patients besides the patient from whom the stored specimen was obtained. In a first example, a microscopic portion of stored tissue having a specific microscopic phenotype is retrieved from a biobank for the benefit of a second patient, who is a different individual from the patient from whom the stored sample was derived. In this case, if a new patient comes in, and a tissue biopsy is performed, then it may be of interest to locate a past case where a similar microscopic phenotype was presented. The disclosed system will permit such retrieval based on a histological image from the new patient. Once the section, and a small region of the section, has been retrieved for the original patient, then this can be subjected to molecular testing, e.g., to determine whether the same molecular pathology is present and, if so, to look at the therapy and/or prognosis of the previous patient as a guide for the current patient.

In a second example, the invention can be applied for the purpose of performing an analysis of a population of patients who share a particular microscopic phenotype. To do this, the researcher defines the microscopic phenotype on one sample, and the invented system is used to retrieve bits of tissue from the best-match identified sections of specimens taken from each of a larger population of patients. The analysis can be, e.g., a molecular analysis, e.g., genomic, proteomic, or transcriptomic analysis; or e.g., a metabolically active analysis, e.g., an enzymatic analysis or an analysis of cellular metabolism. In other embodiments, the extracted, retrieved portions of specimen are subjected to a set of molecular tests and population analysis to ask, e.g., whether a given population has a distinctive molecular signature or pathology.

As used herein, the terms "micro-structure," "microstructural phenotype," and "microscopic phenotype" refer to a value based on a quantitative measure derived from one or more histological characteristics visible in a microscopic image of tissue that has been subjected to one or more histological stains. Without limitation, such micro-structural phenotypes may include the number, morphology, types and spatial distribution of cells in a particular localized region of tissue, such as within a region of diameter about 100 microns, although regions as small as 10 microns or as large as the entire section could be of interest. The value of the phenotype can be a quantitative measure (number), a qualitative or subjective property (low/high), or a name for a type of the characteristic (lung cancer cell).

Accordingly, in one aspect the invention features a series of planar sections cut from a solid biological sample, which includes: a) planar sections cut sequentially from a solid biological sample; b) a two dimensional coordinate system co-planar to each of the sections to allow for spatial localization of features identified on the sections; and c) a third dimensional coordinate system perpendicular to the sections to allow for ordered, sequential sections.

Each of the sections can be mounted on a support. As discussed above, a tape is adhered to the face of the specimen blockface, so that when the microtome knife blade cuts a thin section from the specimen, the thin section is thereby transferred to a tape. The tape can itself serve as this support for the purposes of the invention. Alternatively, the section can be transferred from the tape to another support, as detailed herein.

In one embodiment, the solid biological sample is embedded in an embedding medium, and the two dimensional coordinate system is embedded in the embedding medium surrounding the solid biological sample. As used herein, "embedding" is the process of sealing a specimen in a supporting medium in order to keep it intact during cutting of thin sections using a microtome. The medium can be paraffin wax-based or plastics-based such as epoxy resins, or mixtures. Embedding mediums are firm media known to those of skill in the art, such as, e.g., paraffin, wax, polyester wax, paramat, Polyfin™ (Electron Microscopy Sciences, Hatfield, Pa.).

The specimen block can be equipped with fiducial elements from which can be determined a coordinate system rigidly attached to the specimen. The fiducial elements can be inserted into and through the entire specimen block, so that the fiducial elements are integral to the specimen block, and thus integral to any section cut from the specimen block.

In another embodiment, the two dimensional coordinate system is marked on the support.

The series of planar sections cut from a biological sample can further include a) at least one analyzed section for undergoing feature identification and location; and b) an unprocessed section for storage without undergoing the feature identification and location and having availability for future retrieval and analysis.

The series of planar sections cut from the solid biological sample can further include: d) a spatial index associated with the sample and including a listing of the identified features and a spatial localization of the identified features on the ordered, sequential sections to provide a three dimensional topographical representation for the sample.

Another aspect of the invention features a set of sections of a solid sample, which includes: a) at least one analyzed section for undergoing feature identification and location; b) an unprocessed section for storage without undergoing the feature identification and location and having availability for future retrieval and analysis; c) a two dimensional coordinate system on the sections to allow for spatial localization of features identified on the at least one analyzed sections; d) a third dimensional coordinate system across the sections to allow for ordered, sequential sections; and e) a spatial index associated with the sample and including a listing of identified features and the spatial localization of the identified features on the ordered, sequential sections, wherein the spatial index provides a pointer to a location on the unprocessed section in response to a query. Because the sections are in tight registry, in each of the sections of the set of sections the two-dimensional coordinate system can be superimposed on each adjacent section.

In another aspect, the invention features a three-dimensional representation of a sample, which includes a) digital images of a set of ordered, sequential sections cut from a solid sample, wherein the sections each have a two dimensional coordinate system to provide for spatial localization of features identified on the sections and a third dimensional coordinate system across the sections to allow for ordered, sequential sections; and b) a spatial index associated with the sample, the spatial index including references to the identified features and the spatial localization of the identified features on the ordered, sequential sections.

In yet another aspect, the invention features a system for retrievably storing a set of planar sections cut from a solid specimen, including: a) a sequence of unprocessed planar sections cut from the specimen; b) a spatial index associated with the specimen, the spatial index including (i) reference to a two dimensional coordinate system, the two dimensional coordinate system being co-planar with each of the sections to allow for spatial localization of features identified on the sections; (ii) reference to a third dimensional coordinate system perpendicular to the sections to allow for sequential ordering of the sections; (iii) a listing of identified features on each the section; and (iv) a spatial localization of each the identified feature as a function of the two dimensional coordinate system and the third dimensional coordinate system. In some instances, the planar sections can be stored on a tape support. The system for retrievably storing a set of planar sections can further include a sequence of processed planar sections cut from the specimen, wherein the sequence of processed sections is a subsequence of a combination of the sequence of unprocessed sections and the sequence of processed sections.

In a method of retrievably storing a three-dimensional specimen block containing a microscopic region of interest, the method includes: a) mounting a specimen block on a microtome so as to expose the specimen blockface; b) establishing a two dimensional coordinate system co-planar to each of the sections to allow for spatial localization of features identified on the sections; c) establishing a third coordinate system z perpendicular to the blockface, the third coordinate system z including a set of ordered, iterative, sequential sections of the specimen, the set of sections prepared by: i) adhering a support to the exposed specimen blockface; ii) cutting a thin section from the exposed specimen co-planar with the blockface, and removing from the blockface the thin section attached to the support thereby producing a support-mounted section having two dimensional (x,y) coordinates co-planar with the support and having a support side and a section side; iii) repeating steps (i) and (ii) for at least z times; and iv) with each repetition of (i) and (ii) above, retaining the support-mounted sections in sequential order of z=1→z=n to preserve a series of support-mounted sections; d) dividing the series of sections into at least two sub-series, and processing at least one of the sub-series to identify features of the specimen, and whereby a second of the at least two sub-series remains unprocessed; and e) storing the sections in a retrievable storage system.

In the method of retrievably storing a three-dimensional specimen block containing a microscopic region of interest, the specimen can be equipped with at least three fiducial elements to establish the two dimensional (x,y) coordinate system co-planar with the blockface. Alternatively, or in addition to, the support is labelled with a set of coordinate points to establish the two dimensional (x,y) coordinate system co-planar with the blockface. The adhered support can be a tape, or can be another type of support such as a glass or plastic slide. The support is adhered to the section by a chemical adhesive, or by a static property, or by other adhering properties known to those skilled in the art. The support can be labelled with the value n of the third coordinate system z.

In the method of retrievably storing a three-dimensional specimen block containing a microscopic region of interest, the method further includes transferring the section from the tape to a glass slide. Optionally, this can include a) placing the section side of the tape-mounted section on a glass slide coated with an ultraviolet-light curable polymer; b) curing the polymer with ultraviolet light; and c) removing the tape from the section.

In the method of retrievably storing a three-dimensional specimen block containing a microscopic region of interest, the two dimensional coordinates (x,y) of a section z=n are in alignment with the two dimensional coordinates (x,y) of a section z=n+1.

Referring to step d) dividing the series of sections into at least two sub-series, and processing at least one of the sub-series to identify features of the specimen, the processed sub-series can be treated histologically. Processing the sub-series to identify features of the specimen can further include digital imaging of each section of the sub-series, and also further include analyzing each section of the sub-series to reveal microscopic phenotypic information and cellular features.

A method for feature-based retrieval of a portion of a specimen includes a) developing a catalog of features in the specimen based on analysis of portions of the specimen according to the method of retrievably storing a three-dimensional specimen block containing a microscopic region of interest set forth above; b) developing a spatial index of the cataloged features in the specimen; and c) retrieving the portion of the specimen based on a selected feature and with reference to the spatial index, wherein the selected feature is associated with a cataloged feature in the specimen, wherein at least one of the analyzed portions of the specimen is associated with the cataloged feature, and wherein the retrieved portion of the specimen is different from the at least one of the analyzed portions of the specimen that is associated with the cataloged feature.

In method for feature-based retrieval of a portion of a specimen, the retrieved portion of the specimen is proximal to the at least one of the analyzed portions of the specimen.

In method for feature-based retrieval of a portion of a specimen, the retrieved portion of the specimen further includes retrieving a portion of the specimen that has not undergone analysis but, based on the spatial index, is nearest to the at least one of the analyzed portions of the specimen that is associated with the cataloged feature.

The method for feature-based retrieval of a portion of a specimen can further include: a) cutting the specimen into sections and associating the spatial index with the sections in order to develop ordered sections; b) identifying a set of features including the cataloged feature for a first section in the ordered sections; c) storing the first section and information related to the set of features; d) matching the selected feature with the cataloged feature; e) identifying the first section with reference to the spatial index and the cataloged feature; f) identifying a second section proximal to the first section but that has not undergone analysis; and g) retrieving the second section. The method for feature-based retrieval of a portion of a specimen can further include extracting a first aliquot from the retrieved portion of the specimen. This method can also further include a) retrieving a second portion of the specimen with reference to the spatial index, wherein retrieving the second portion is based on an absence of the selected feature in the second portion; and b) extracting a second aliquot from the second retrieved portion of the specimen to operate as a baseline in analyzing the first portion.

A method of preparing a series of sections of a specimen includes a) mounting a specimen block on a microtome so as to expose the specimen blockface; b) establishing a two dimensional coordinate system co-planar to each of the sections to allow for spatial localization of features identified on the sections; c) establishing a third coordinate system z perpendicular to the blockface, the coordinate system including a set of ordered, iterative, sequential sections of the specimen, the series prepared by: i) adhering a support tape to the specimen blockface; ii) cutting a thin section from the specimen co-planar with the blockface, and removing from the blockface the thin section attached to the support tape thereby producing a tape-mounted section having two dimensional (x,y) coordinates; iii) repeating steps (i) and (ii) for at least z times; and iv) with each repetition of (i) and (ii) above, retaining the tape-mounted sections in sequential order of z=1→z=n to preserve a series of tape-mounted sections. In the method of preparing a series of sections of a specimen, the specimen is equipped with at least two fiducial elements to establish the two dimensional (x,y) coordinate system co-planar with the blockface. Alternatively, or in addition to, the support can be labelled with a set of coordinate points to establish the two dimensional (x,y) coordinate system co-planar with the blockface.

The invention further includes a series of planar sections cut from a solid biological sample, including: a) planar sections cut sequentially from a solid biological sample; b) a two dimensional coordinate system co-planar to each of the sections to allow for spatial localization of features identified on the sections; and c) a third dimensional coordinate system perpendicular to the sections to allow for ordered, sequential sections, wherein the series of planar sections is prepared by the method of preparing a series of planar sections described in the paragraph above. The series of planar sections further includes a) at least one analyzed section for undergoing feature identification and location;

and b) an unprocessed section for storage without undergoing the feature identification and location and having availability for future retrieval and analysis, also prepared by the method of preparing a series of planar sections described in the paragraph above.

In one aspect is disclosed a series of sections of a sample, including a) a two dimensional coordinate system on the sections to allow for spatial localization of features identified on sections; b) a third dimensional coordinate system across the sections to allow for ordered, sequential sections; and c) a spatial index associated with the sample and comprising a listing of the identified features and the spatial localization of the identified features on the ordered, sequential sections to provide a three dimensional topographical representation of the sample. In another embodiment, the series of sections of a sample can further include a) at least one analyzed section for undergoing feature identification and location; and b) an unprocessed section for storage without undergoing the feature identification and location and having availability for future retrieval and analysis.

In another aspect is disclosed a set of sections of a sample, which includes a) a two dimensional coordinate system on the sections to allow for spatial localization of features identified on sections; b) a third dimensional coordinate system across the sections to allow for ordered, sequential sections; and c) a three dimensional topographical representation of the sample comprising a spatial index associated with the sample, the spatial index comprising references to the identified features and the spatial localization of the identified features on the ordered, sequential sections.

In another aspect is disclosed a three-dimensional representation of a sample, comprising: a) a set of ordered, sequential sections cut from the sample, wherein the sections have a two dimensional coordinate system to provide for spatial localization of features identified on the sections; and b) a spatial index associated with the sample, the spatial index comprising references to the identified features and the spatial localization of the identified features on the ordered, sequential sections.

In another aspect is disclosed a set of sections of a sample, comprising: a) at least one analyzed section for undergoing feature identification and location; b) an unprocessed section for storage without undergoing the feature identification and location and having availability for future retrieval and analysis; c) a two dimensional coordinate system on the sections to allow for spatial localization of features identified on the at least one analyzed sections; d) a third dimensional coordinate system across the sections to allow for ordered, sequential sections; and e) a spatial index associated with the sample and comprising a listing of identified features and the spatial localization of the identified features on the ordered, sequential sections, wherein the spatial index provides a pointer to a location on the unprocessed section where a first identified feature is likely to occur, in a future analysis of the unprocessed section.

In another aspect is disclosed a set of sections of a sample, comprising: a) at least one analyzed section for undergoing feature identification and location; b) an unprocessed section for storage without undergoing the feature identification and location and having availability for future retrieval and analysis; c) a two dimensional coordinate system on the sections to allow for spatial localization of features identified on the at least one analyzed sections; d) a third dimensional coordinate system across the sections to allow for ordered, sequential sections; and e) a spatial index associated with the sample and comprising a listing of identified features and the spatial localization of the identified features on the ordered, sequential sections, wherein the spatial index provides a pointer to a location on the unprocessed section where a first identified feature is located on a proximal analyzed section.

In yet another aspect is disclosed a method for feature-based retrieval of a portion of a sample, comprising: a) cataloging features in the sample based on analysis of portions of the sample; b) developing a spatial index of the cataloged features in the sample; and c) retrieving the portion of the sample based on a selected feature and with reference to the spatial index, wherein the selected feature is associated with a cataloged feature in the sample, wherein at least one of the analyzed portions of the sample is associated with the cataloged feature, and wherein the retrieved portion of the sample is different from the at least one of the analyzed portions of the sample that is associated with the cataloged feature. In some embodiments of the method, the retrieved portion of the sample is proximal to the at least one of the analyzed portions of the sample. This method can further include retrieving the portion of the sample that has not undergone analysis but, based on the spatial index, is nearest to the at least one of the analyzed portions of the sample that is associated with the cataloged feature.

In other embodiments of the aforesaid method, the method further includes a) cutting the sample into sections and associating the spatial index with the sections in order to develop ordered sections; b) identifying a set of features including the cataloged feature for a first section in the ordered sections; c) storing the first section and information related to the set of features; d) matching the selected feature with the cataloged feature; e) identifying the first section with reference to the spatial index and the cataloged feature; f) identifying a second section proximal to the first section but that has not undergone analysis; and g) retrieving the second section.

Optionally, the method can further include extracting a first aliquot from the retrieved portion of the sample. In some cases, the method also further includes a) retrieving a second portion of the sample with reference to the spatial index, wherein retrieving the second portion is based on an absence of the selected feature in the second portion; and b) extracting a second aliquot from the second retrieved portion of the sample to operate as a baseline in analyzing the first portion.

BRIEF DESCRIPTION OF THE DRAWINGS

The accompanying drawings, which are incorporated in and constitute a part of this specification, illustrate one (several) embodiment(s) of the invention and together with the description, serve to explain the principles of the invention.

FIG. 3A is a diagrammatic representation of a process for archiving sections on which features have been identified and mapped, and matching features on a test sample with features from the archived sections;

DETAILED DESCRIPTION

Figure 1A:
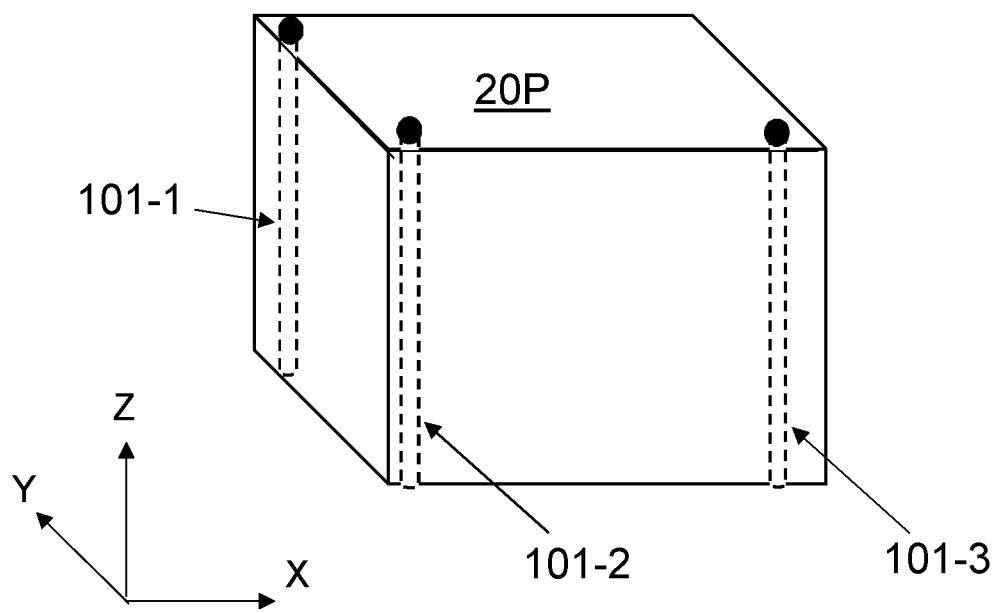
FIG. 1A is a perspective side view of one embodiment of the present invention, showing fiducial elements embedded into a block of a biological tissue sample.

The invention is directed to a preserved serial set of sequential, iterative, and ordered thin sections of a specimen block, and a catalogue of images taken from one or more sub-series of the set of sections and organized so as to create a three-dimensional profile of the microscopic structures of the specimen block. The serial set of sequential, iterative, and ordered thin sections are prepared from the specimen block by cutting and imaging thin sections of that specimen block so that the thin sections remain strictly in the sequential, iterative, order in which they are cut from the specimen block. A spatial index is created from the catalogued three-dimensional images which is searchable by local content-based image retrieval (LCBIR). The LCBIR query is used to locate, within the three-dimensional index, microscopic structural features, thereby making that portion of the specimen available for further analysis and/or for extraction. The procedure is summarized as follows.

First, one obtains a specimen block which is suitable for sectioning by microtome. The specimen block is equipped with fiducial elements from which one can determine a coordinate system rigidly attached to the specimen. The fiducial elements can be inserted into and through the entire specimen block, or can be attached to the outside of the specimen block, as described more fully below.

In those situations where the fiducial element is only on the outer surface of the specimen block, the coordinate system defined by the fiducial elements is referred to as "coordinate system A." The set of supports on which the sections are mounted are pre-printed with a second set of visible fiduciary marks to provide another set of coordinate axes referred to as "coordinate system B." When imaging the first series of sections, the image area should include the fiduciary marks of coordinate system B. Since coordinate systems A and B are in rigid registry, B can substitute for A. In the subsequent steps, coordinate section B will be used to localize a spatial point on an unprocessed section from the blank series (the biobanked series of blank tissue sections).

The specimen block (with fiducial elements integral thereto) is cut into a series of thin sections using a microtome. Sections can be as thin as 1 to 5 micrometers ($\mu m$), but are more typically in the range of 10, 15, or 20 $\mu m$, to 100 $\mu m$, or even 200 $\mu m$ in thickness. Each cut section is transferred to a planar support. The planar support is preferably transparent, but, depending on the type of staining and imaging employed, can be translucent or even opaque. In some embodiments, the support is a glass slide. Transfer of each cut section to the support is facilitated using a technique referred to as "tape transfer," whereby, following each iteration of the microtome blade, a piece of adhesive tape is transferred to the blockface of the specimen block mounted on the microtome, which is the surface of the specimen block exposed to the knife blade of the microtome. See, e.g., U.S. patent application Ser. No. 62/187,114, filed Jun. 30, 2015, hereby incorporated by reference.

Thus, each newly cut section is released from the specimen block attached to its own piece of tape. The tape serves as a carrier to ferry the cut sections from the cutting region (e.g., the knife blade) of the microtome to a planar support such as a glass microscope slide. Thin sectioning with the tape transfer technique prevents the shape of the thin section from becoming distorted, and thus preserves the precise geometrical structure from one section to the next. The tape and/or support are labelled with a number (z), such that thin section $z=1$ is the first thin section cut from the specimen block, and, in the sequence $1 \rightarrow n$, thin section $z=n$ is the $n^{th}$ section cut from the specimen block.

The series of thin sections are divided into at least two sub-series. The first sub-series of sections is subjected to histological treatment, and subsequently imaged and analyzed to reveal microscopic phenotypic information and various cellular features. Additional sub-series can be histologically treated with varying stains and detectable tags. Finally, at least one sub-series of sections, suitably interleaved with the histologically treated sections, is left unprocessed on the support, either on the tape itself, or on a glass slide support, and stored (a.k.a., "banked").

The histologically treated sub-series of stained sections, after imaging, are subjected to image processing algorithms in order to define feature vectors $F(x,y)$ at each spatial location $(x,y)$ within the plane of the section which is co-planar with the support. A third coordinate, the z coordinate, is defined from the serial number of the section. Tape transfer assisted sectioning methods make feasible keeping track of the z-coordinate. Thus, at the end one has a feature vector $F(x,y,z)$ for each point in the three dimensional specimen. In addition, the de-identified patient record number will be called P. Thus, one obtains a set of feature vectors $FP(x,y,z)$.

These feature vectors are stored in a database, together with information which allows precise association with the banked, unprocessed sections. Like the histologically treated sections, the unprocessed sections also have well defined locations $(x,y,z)$ associated with them through the coordinate system or systems, with the z-coordinate corresponding to the serial section number, and the de-identified patient record number P. The features are searchable using Local-Content-Based-Image-Retrieval (LCBIR).

The next step is a query-retrieval system. In this step, a new section of tissue (e.g., from a new patient) is histologically processed, using the same or similar histological processing that was used when making the samples stored in the biobank. This new section is examined for some feature associated with a spatial location (e.g., a specific region contained within a tumor, such as, e.g., containing specific cell types as specified by morphology or histochemical stain). This processed section is imaged, and subjected to the same image processing method used to create the spatial index, to determine a feature vector FQ(x',y'), where Q denotes 'query'.

The database associated with the specimen bank is then searched by content-based searching to obtain a best match between the query feature vector $F_Q(x',y')$ and a feature vector stored in the database. By way of example, if the best matched feature vector is $FP_B(x_B,y_B,z_B)$, where $P_B$ corresponds to a specific patient record, and $(x_B,y_B,z_B)$ is the best matched physical location in the banked tissue. This determines a specific thin section, and a specific spatial location $(x_B,y_B,z_B)$ on that thin section, which potentially contains a match to the specific location in the new sample. The pair of coordinates $(x_B,y_B)$ denotes the 2D coordinates within that specific section, and $z_B$ is the z-coordinate associated with the same section.

In some cases, where it is desired to extract a small portion of sample from the specimen block, a successful retrieval will aid in precise phenotypic selection of a tissue sample that is more accurate than available from patient medical records only, or only from a histochemical stain on a nearby section but without the ability to precisely spatially localize the tissue micro-region of interest.

Methods and Materials

Specimens. Specimens which can be analyzed, stored, and retrieved by the methods of the invention include materials that are suitable for labeling with a fiducial element and cutting into thin sections with the use of a microtome. Such materials can be either inorganic (e.g., geological or industrial, such as a part or component with internal structure that is being subjected to reverse engineering by cutting into thin sections and subsequent imaging), or organic. Organic materials can be botanical (plant), fungal, or animal materials. In certain embodiments, the specimen is a mammalian tissue, such as those of animals commonly used in research, such as rodents (e.g., mice or rats), rabbits, dogs, and primates. Other suitable mammalian tissues are also those of animals commonly treated in a veterinary or human clinical setting. Specimens can be normal tissue specimens or pathology specimens, such as those obtained during clinical trials, during a biopsy, and/or during surgery.

Tissue Preservation. Materials suitable for use in the systems and methods described herein typically undergo some form of preservation in advance of sectioning. Where the material is a biological tissue, the tissue is often preserved before sectioning by freezing the tissue as a tissue block, or by embedding a block of tissue in paraffin. Optionally, the tissue can be perfusion fixed or immersion fixed tissue.

Preservation of tissue samples can be by freezing or by embedding the tissue in paraffin. Techniques for cryo-protection and freezing of tissue into tissue blocks have been described. See., e.g., Pinskiy et al., "A low-cost technique to cryo-protect and freeze rodent brains, precisely aligned to stereotaxic coordinates for whole-brain cryosectioning," *Journal of Neuroscience Methods*, vol. 218, pages 208-213 (2013). For methods of preparing paraffin-embedded tissue blocks, see Haines, et al., "Technical considerations for developing enzyme immunohistochemical staining procedures on formalin-fixed paraffin-embedded tissues for diagnostic pathology." J Vet Diagn Invest, 1991. 3(1):101-12. Other embedding materials include resins and rubber. Frozen sections can also be embedded (Simonetti et al., J. Neuroscience Methods, 158:242-250 (2006)).

Fiducial elements. Where specimens are embedded in another material, e.g., paraffin or rubber or another suitable freezing/embedding medium, fiducial elements can be added to the tissue block outside of the specimen resulting in extrinsic registration without damage to the specimen. In embodiments in which specimens are not embedded in another material (the specimen itself being cut into blocks and infiltrated with a hardening substance), fiducial elements can be added to the tissue block itself, with only minimal damage to the specimen. One method is to place external fiducial markers by placing three parallel needle tracks in at least three, preferably four, spaced apart locations in the embedding material, and filling the needle tracks with a marker solution, e.g., an acrylamide solution mixed with Indian ink and, optionally, a radioactive component (Simonetti et al., J. Neuroscience Methods, 158:242-250 (2006); Bussolati et al., "Tissue arrays as fiducial markers for section alignment in 3-D reconstruction technology," *J. Cell. Mol. Med.*, 9(2):438-445 (2005)).

To further avoid distortion or damage to the specimen by the fiducial element, a fiducial element can be applied solely to the facing surface of the specimen block (hereafter referred to as "coordinate system A"). Extrinsic markers can be used either inside or outside the tissue sample. Simonetti et al., J. Neuroscience Meth., 158:242-250 (2006). Registration is extended to sections cut from the interior of the specimen by a second set of coordinate points ("coordinate system B") which are printed on the support, i.e., on the slide or tape to which the cut section is transferred prior to imaging and digitization.

One exemplary marker solution for forming a fiducial element system in a frozen sample is made of 950 microliters of an 8% acrylamide solution mixed with 25 microliters of Indian ink and 18 microliters of iodo[14C]antipyrine solution (25 Ci/ml). Other colorants may also be added if staining is desired. Three microliters of ammonium persulfate (APS, 30%) and 3 microliters TEMED (N,N,N',N'-tetramethylethylenediamine) are be added before the marker solution is sucked into a 1 milliliter (ml) syringe equipped with a needle and a p10 catheter (outer diameter 0.61 mm). Within one minute after the APS is added, the syringe is pushed inside each track until it reaches the bottom of the chuck, after which solution is gently pushed out of the syringe. The acrylamide solution is allowed to polymerize for 5 minutes, after which the block can be stored at −80° C. Additional methods of embedding a fiducial element in specimens and imaging therefrom are described in, e.g., Simonetti et al., J. Neuroscience Meth., 158:242-250 (2006).

Each specimen is cut serially into sections of uniform thickness and transferred to a support by tape transfer. Materials useful as supports are glass slides, e.g., glass microscope slides; pieces of tape, e.g., a polyimide tape such as Kapton® tape (made from Kapton® HN general purpose film available from E.I. du Pont de Nemours and Company (Wilmington, Del.), or CryoJane® tape, made available from Leica Biosystems of Richmond, Ill.

Suitable materials for use as a support can also include plastic supports, metal frame mounted polyethylene terephthalate (PET) membrane slides, and metal-framed polyethylene naphthalate (PEN) membrane slides. Golubeva et al., PLOSone June 2013

Tape transfer method. This system relies on the use of an adhesive tape made, preferably, from a polyimide film, more preferably from poly-oxydiphenylene-pyromellitimide, which in commercially available form is called Kapton® (Dupont de Nemours and Company, Wilmington, Del.). The tape is adhered onto the blockface using a roller by either manual or mechanical methods. As the block passes across the knife, the tape remains attached to, or adhered to, the surface of the resulting section so as to prevent the tissue section from deforming. It is an object of the invention that the shape of the tissue section remain true to the shape of the original specimen, and thus that the cut tissue section not be deformed, mutilated, malformed, misshaped, disproportioned, disfigured, truncated, blemished, or marred; nor distorted, twisted, warped, or irregular relative to the parameters of the original specimen.

Post-sectioning, the tape/section complex is placed onto a coated glass slide. The slide is pre-coated with a UV polymer; suitable polymers are described in U.S. Pat. No. 5,444,105, "Specimen mounting adhesive composition", issued Aug. 22, 1995, hereby incorporated by reference.

Adhesion between the tissue section and the coated glass slide is achieved by exposure to ultraviolet light (UV). When UV light is applied, the polymer is cured, resulting in a firm adhesion of the section onto the slide. The adhesion between section and slide is greater than that of the adhesion between the section and the adhesive tape, allowing the operator to peel the tape away from the section without damaging the section. After removal of the adhesive tape, the glass slides can be stained. This process is repeated for all sections cut from the block. The curing reaction can be performed once per slide, after all sections have been adhered onto the slide. A commercial embodiment of tape transfer based sectioning is available (CryoJane® Tape-Transfer System (developed by Instrumedics, Inc., and now available from Leica Microsystems Inc., Buffalo Grove, Ill.)).

Tape transfer can be achieved manually according to manufacturer instructions. In certain embodiments, tape transfer is achieved by an automated method; see, e.g., U.S. Patent Application Ser. No. 62/187,114, filed Jun. 30, 2015, hereby incorporated by reference.

Identifiers. Each thin section on a support is indexed with a unique set of identifiers. The first set of identifiers is one or more items of metadata. The metadata helps to organize electronic resources, provide digital identification, and support archiving and preservation of specimens. Useful types of metadata include date and time of specimen collection, tissue type, sample preparation related data, cross-indexing with de-identified patient medical records containing diagnostic, therapeutic, prognostic and outcome information, information about other specimens or samples from the same patient.

Each section is associated with a numerical value (n) representing the sub-series of thin sections to which it belongs. By way of example, a given specimen block is cut into a series of three sub-series of thin sections. The first series (n=1) is the first section cut plus each third section thereafter. The second series (n=2) is the second section cut plus each third section thereafter. The third series (n=3) is the third section cut plus each third section thereafter.

Each cut section is further associated with a z coordinate value. As the specimen block is cut by the microtome, the first section cut from the microtome is assigned a z value of 1, the second cut section is assigned a z value of 2, the third cut section is assigned a z value of 3, and so on. Assuming uniformity of thickness of section cutting, the depth into the specimen block of any particular thin section, i.e., the distance between a thin section and the initial blockface, is the z value times the thickness of each cut section. By way of example, when cutting 10 micrometer sections, the $i^{th}$ section represents tissue taken z·i micrometers deep into the specimen block.

In certain embodiments, a glass slide or other specimen mount may have affixed to it a pre-printed and bar-coded label with the z-coordinate number to be assigned to the section to which the tape becomes affixed. It is further preferable that each such label be pre-printed with the n value of the sub-series to which the section will be assigned. The label bar-code can be used for asset tracking, i.e. physically identifying the slide to which the labeled barcode is attached. The support, e.g., tape, glass slide, or other support, whether by bar code label or numerical printing, can have affixed to it any of the above indicated z, n, (x,y) or other coordinate values, metadata identifiers, patient record numbers, de-identified patient record numbers, or any other information important to the archiving or retrieval of specific specimens or portions thereof.

Histology. Each of the sub-series of thin sections which are to be imaged (i.e., all sub-series with the exception of the sub-series of "blank" specimens) are treated to enhance digital imaging of particular features within the specimen. Treatments include histology and histochemical stains, radiography, or treatment with tagged antibodies or receptors, or treatment with tagged molecules capable of complementary pairing, e.g., DNA or RNA molecules. By way of example, useful histology stains include hematoxylin and eosin (H&E) stains, uranyl acetate, lead citrate, safranin, oil red O, Congo red, fast green FCF, toluidine blue, trichrome stains, Wright's stain, Orcein stain, and silver salts. Histochemical stains include Perls Prussian blue. Radiographic techniques can be used when coupled with steps of X-ray and autoradiography prior to digitization. Staining with tagged molecules can include, e.g., avidin biotin staining, direct immunoenzyme staining, and indirect immunoenzyme staining. Also useful in the methods of the invention are florescent tags and colloidal gold. Preferably, specimens are treated with the nissl method, the Golgi method, ion-eriochrome cyanine, and luxol fast blue MBS (Kluver H, et al., A method for the combined staining of cells and fibers in the central nervous system, J Neuropathol Exp Neurol, 1953, 12:400-403; Page, K. M. A stain for myelin using solochrome cyanin, J Med Lab Technol, 1965, 22:224-225).

With the exception of blank sections, each sub-series of sections is treated with a different histology stain or tag. By way of example, for a specimen block which is cut into three series of thin sections, the first series (n=1) can be stained with H&E stain, the second series (n=2) can be treated with nissl stain, and the third series (n=3) can be left blank.

Imaging and Digitization. Specimens on glass slides are photo-optically scanned at high speed to produce high-definition digital images of the specimen. Imaging can be transmitted (brightfield) and reflected (fluorescence) light microscopy imaging. Preferably, imaging is done using a whole-slide microscopic instrument. In one embodiment, digital imaging can be performed with commercially available equipment. One non-limiting example is the NanoZoomer® 2.0 HT (Hamamatsu Photonics K.K., Hamamatsu, Japan).

Microscopic phenotypic information and features include spatial distribution of cells of specific morphologies or exhibiting specific stains; boundary regions of a tumor; and other tissue elements such as cross sections of blood vessels, neuronal processes, or any other characteristic microscopic elements of tissue that may undergo pathological alteration.

Specimen Depository. Specimens on supports are retained for preservation in storehouses variously referred to as depositories, repositories, banks, biobanks, or tissue banks. Within the depository, the location of each support is indexed so that each specific specimen can be retrieved. Preferably, the supports are stored in a storage unit, such as a tray, which is in operable communication with a carrier within an automated storage system. When a slide is requested by an operator, the system delivers the particular slide to the operator. A non-limiting example of a system for storing specimens on supports include The Anatomic Pathology Slides Storage System (Southwest Solutions Group®, Lewisville, Tex.). Depository services are also provided by Iron Mountain, Inc. (Boston, Mass.). See, e.g., US2013/0319914, "Organizing pathology assets", hereby incorporated by reference.

Queries/algorithms for searching. The series of sections which are treated with stains or tags, after imaging, are subjected to image processing algorithms in order to define feature vectors F(x,y) at each spatial location (x,y) within the plane of the section. The spatial index created using the multiple sub-series of sequential, iterative, and ordered thin sections disclosed herein is particularly suited to Localized Content Based Image Retrieval (LCBIR), which is also known as Local Query by Image Content (LQBIC) and Local Content-Based Visual Information Retrieval (LCB-VIR). "Content-based" means that the search analyzes the contents of the image rather than the metadata (metadata being keywords, tags, identifiers or descriptions associated with the image). The term "content" in this context refers to colors, shapes, textures, or any other information that can be derived from the digitized stained image, which are indicative of microstructures in the corresponding segment of the specimen. LCBIR is a CBIR task where the user is only interested in a portion of the image, not a global or holistic view of the image. Rahmani et al., "Localized Content Based Image Retrieval", Abstract, *MIR'05*, Nov. 10-11, 2005, Singapore; Ma, Ziping, et al., Translation and scale invariants of Legendre moments for Images Retrieval, J. Info. & Comp. sci., 2011, 8(11):2221-2229; Chong, C. W., et al., Translation and scale invariants of Legendre moments, Pattern Recognition, 2004, 37(1):119-129; Teh, C. H. et al., On Image-Analysis by the Methods of Moments. IEEE Transactions on Pattern Analysis and Machine Intelligence, 1988, 10(4):496-513; Kinoshita, S. K., et al., Content-based retrieval of mammograms using visual features related to breast density patterns. J Digit Imaging, 2007. 20(2): p. 172-90; Shyu et al., Local versus Global Features for Content-Based Image Retrieval, IEEE Workshop on Content-Based Access of Image and Video Libraries, 1998.

Retrieval and extraction of features from specimen blanks. As stated above, a sub-series of sections, interleaved with the processed sections, was left unprocessed. The iterative interleaving of the processed and unprocessed series permits each unprocessed section to be characterized microscopically by its proximal, preferably neighboring, more preferably adjacent, processed sections. After the content-based query identifies a thin section indexed according to the best matched feature vector, the support with corresponding unstained physical (U series) section ($z_B$) is then retrieved from storage. A small aliquot of the specimen is extracted from that specimen section (zB), corresponding to the location ($x_B, y_B$). This step is performed by bringing a suitable extraction device in physical contact with the location ($x_B, y_B$) (e.g., a tissue punch, which can be used on a piece of specimen attached to a tape, or a pipette tip, which can be used to extract a small section of specimen from a support). The tissue extraction device tip is positioned using the coordinate system on the tape or slide, using visual guidance and manual movement, or an equivalent automated procedure using a camera to detect position according to the coordinate system and a stepper motor to position the device tip. In another example, the tissue extraction device tip can be positioned with respect to a coordinate system fixed to the glass slide, which has been registered itself to the tissue in accordance with the method described in FIG. 2B, described below.

Other methods of extracting a tissue of interest from a blank specimen are known to those of ordinary skill in the art, including laser capture microdissection, laser-assisted microdissection, laser induced forward transfer, and gravity-assisted microdissection.

The small aliquot of tissue thus extracted is subjected to the desired molecular analysis (e.g., DNA or RNA sequencing).

Figures

Figure 1B:
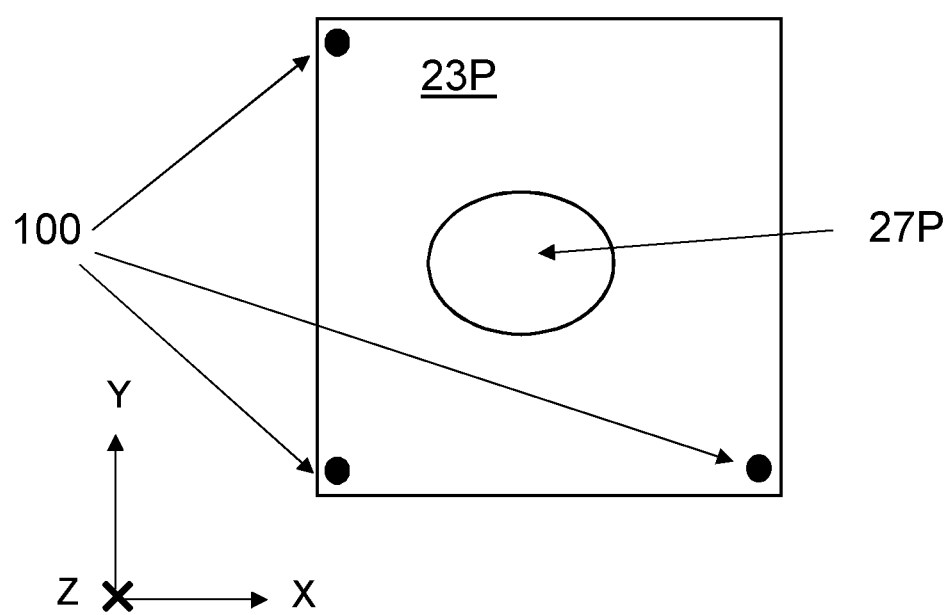
FIG. 1B is a top view of a section cut from the sample block shown in FIG. 1A.

Reference will now be made in detail to the present exemplary embodiments, examples of which are illustrated in the accompanying drawings. Wherever possible, the same or similar reference numbers will be used throughout the drawings to refer to the same or like parts. Symbols used repeatedly are identified as follows:

A Coordinate System A for fiducial system 100
A' Alternative embodiment: mapped coordinate system from coordinate system B
B Alternative embodiment: coordinate system for fiducial element system 210
F Feature
$\{F_{CM}\}$ Best match feature candidate set
$F_{PM}$ Best match feature
$F^1{}_1(x_1, y_1, z_1)$ feature 2 in Section stained with stain 1
$F^1{}_2(x_2, y_2, z_1)$ feature 2 in Section stained with stain 2 (ditto re identifiers)
$F_Q(x', y')$ Test feature
$F_{PM}(x_{PM}, y_{PM}, z_{PM})$ Best match feature vector on a best match section
$F^U{}_{PM}(x_{PM}, y_{PM}, z_{PM})$ Best match feature vector on the unprocessed section associated with the best match section
M Best match
PM Best match patient
P Patient Record number
Q Query
T test
$Z_1$ $1^{st}$ position in sample
$Z_{1 \rightarrow N}$ $1^{st}$ through $N^{th}$ position in sample
$Z_U$ unprocessed position (sometimes $Z_{N+1}$) in sample FIGS. 1A and 1B show a sample block 20P prepared for cutting with a microtome into thin sections. Without limiting the scope of the systems and processes disclosed here to only biological applications, the material contained within the sample block 20P can be a biological tissue embedded in paraffin, or the block 20P may itself be a frozen block of tissue. The letter P is used herein to represent a de-identified patient record number P with which the biological tissue may be associated.

A fiducial element system 100 can be embedded in the block 20P in order to provide reference points on sections cut from the block so that a coordinate system can be established and used for mapping positions on a section. See, e.g., Simonetti et al., "A low temperature embedding and section registration strategy for 3D image reconstruction of the rat brain from auto-radiographic sections," Journal of Neuroscience Methods, vol. 158, pages 242-250 (2006). The fiducial elements can be formed as disclosed above by filling needle tracks in the block with a colored marker solution, or by driving rods of a dark-colored and soft material into multiple locations in the block. The material can be a plastic capable of being sectioned.

The fiducial elements system 100 is shown in FIGS. 1A and 1B to have three fiducial elements 101-1, 101-2, 101-3, in order to provide the three points from which x and y axes can be established for identifying positions in the specimen 27P in a representative section 23P. More fiducial elements can be used, as will be seen in the four fiducial elements 221-1-221-4, inclusive, shown in FIG. 2b. At least three planar fiducial points are required in order to define an x-y coordinate system.

Figure 1C:
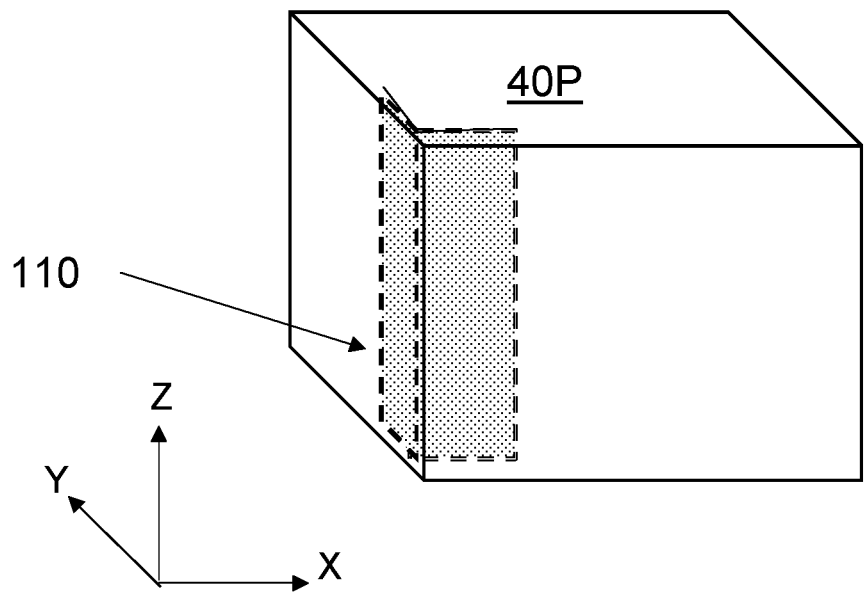
FIG. 1C is a perspective side view of a second embodiment of the present invention, showing a second kind of fiducial elements embedded into a block of a biological tissue sample.
Figure 1D:
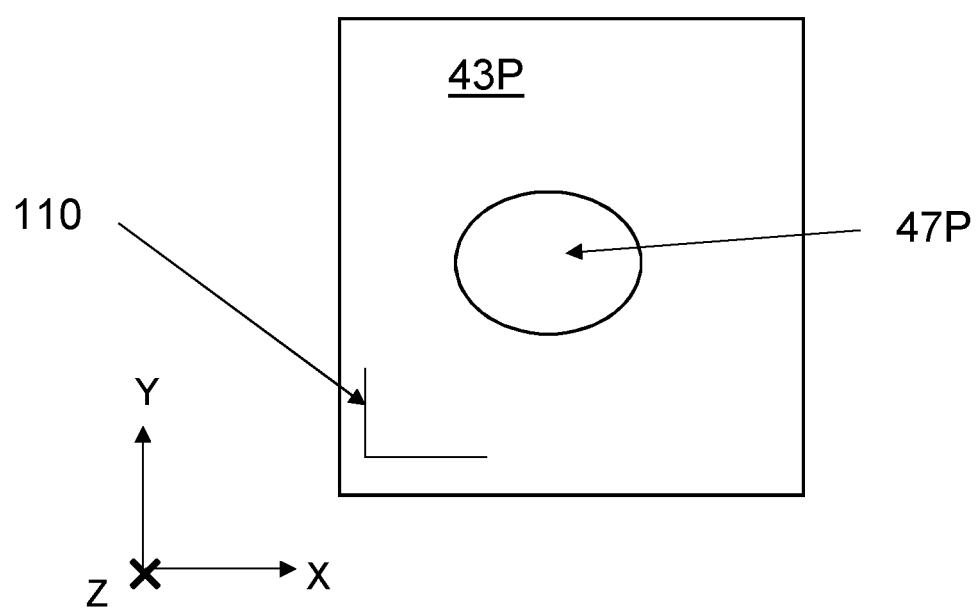
FIG. 1D is a top view of a section cut from the sample block shown in FIG. 1C.

FIGS. 1C and 1D show another sample block 40P from the patient P. A second fiducial element system 110 with two sheets of material or a folded sheet of material, (capable of being sectioned) and embedded in or adhered to adjacent facing surfaces of the block 40P at right angles in order to provide x and y axes themselves on a representative section 43P from which can be established four identifying positions in the tissue 47P in the section 43P. The material can be a dark-colored and soft plastic. Alternatively, the fiducial element system 110 can be formed by cutting an angular channel in the block and filling it with the same colored marker solution.

Figure 2A:
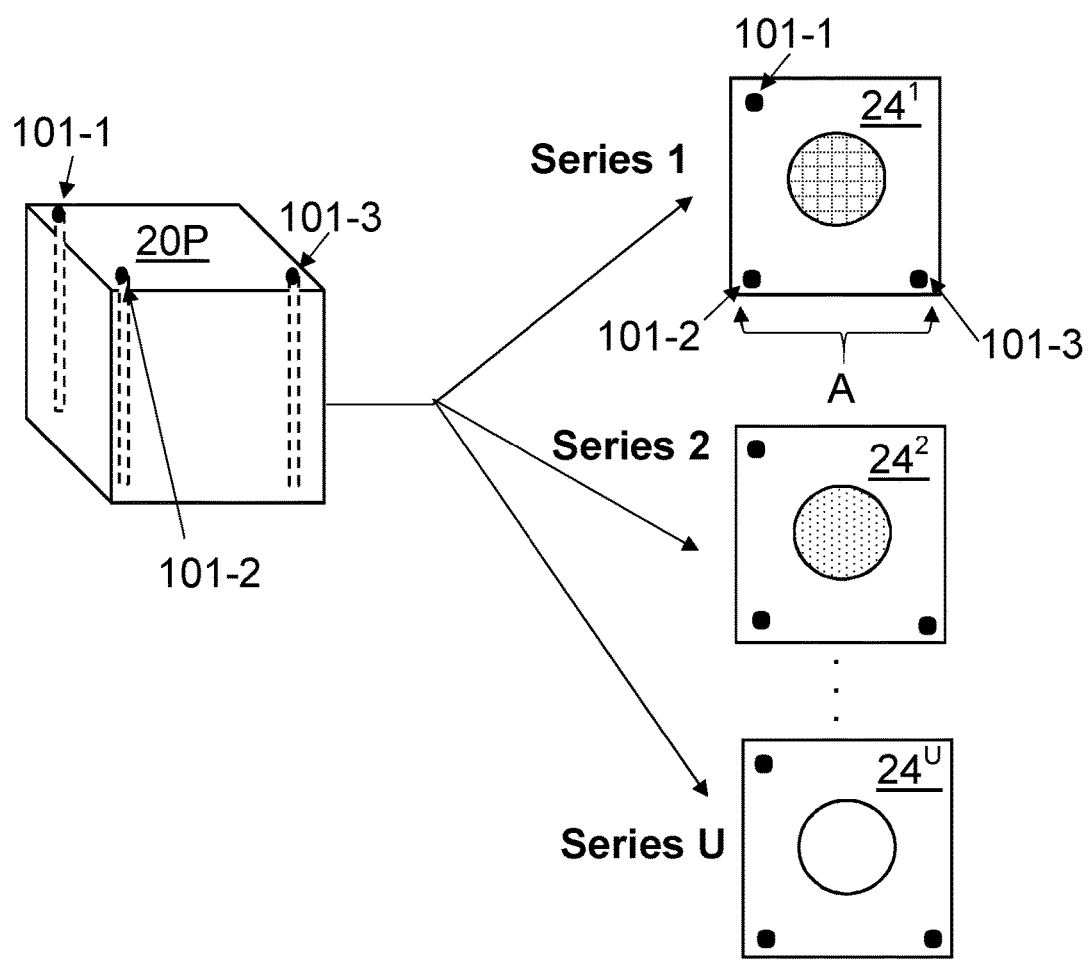
FIG. 2A is a diagrammatic representation of the sample block of FIG. 1A and the cutting of series of sections therefrom.

FIG. 2A is a diagrammatic representation of the sample block 20P from FIG. 1A and the cutting of series of sections therefrom. When they are cut, a record of the order in which the sections were cut from the sample is made and maintained in order to preserve accurate geometrical and proximity information about the sections relative to each other. For example, in the example shown in FIGS. 1A and 1B, sections are cut from the sample along an x-y plane, and a unique cutting order identifier associated with the section can be used to determine where a selected section was cut from the specimen, and how far in the direction of the z coordinate the section was located in the specimen from other sections also identified with a unique cutting order identifier z.

The sections are divided into iterative series in order to conduct different forms of analysis. In one example, the analysis can be conducting histochemical analysis on a section, which is subsequently imaged, to identify microscopic phenotypic information about the portion of the specimen in that section. For example, the information (hereinafter referred to as "features") could be the spatial distribution of cells of specific morphologies or cells exhibiting identifiable characteristics under specific stains.

Multiple series can be defined in order to subject sections to a variety of processing procedures. The example shown in FIG. 2A shows a first series of sections (Series 1, represented by section $24^1$) to be subjected to a first procedure, such as a first stain, and a second series of sections (Series 2, represented by section $24^2$) that is subjected to a second procedure, such as a second stain.

An additional series of sections shown in FIG. 2A (Series U, represented by $24^U$) is left unprocessed or minimally processed and stored away for future use, either on a specimen tape or on a glass slide. The sections in Series U are selected based on the order in which they were cut from the sample so that, were the sections to be organized into the order in which they were cut from the sample, unprocessed sections would be interleaved with the sections to be processed.

The manner of interleaving can be left to the user. As an example, let Z1 represent the position of the first section cut from the sample. A user may choose to create two series, with sections assigned to a series in the order in which they were cut, Series 1 containing sections with positions (Z1, Z3, Z5, Z7, . . . ) and Series U containing sections with positions (Z2, Z4, Z6, Z8, . . . ). Alternatively, the user may choose to create two series, with fewer sections in Series U than in Series 1. For example, Series U may contain sections with positions (Z4, Z8, Z12, . . . ) and Section 2 may contain the rest.

More complicated series definitions can be developed. For example, a user may choose to define multiple series. When three staining protocols are desired, a user may choose to assign sections to a series in the order in which they were cut from the sample, as follows: Series 1: positions (Z1, Z5, Z9, Z13, . . . ); Series 2: positions (Z2, Z6, Z10, Z14, . . . ); Series 3: positions (Z3, Z7, Z11, Z15, . . . ); Series U: positions (Z4, Z8, Z12, Z16, . . . ). A user could also choose to include more sections in one series, or to include more frequent sections into Series U. As an example: Series 1: positions (Z1, Z2, Z7, Z8, Z13, Z14, . . . ); Series 2: positions (Z4, Z10, Z16, . . . ); Series 3: positions (Z5, Z11, Z17, . . . ); Series U: positions (Z3, Z6, Z12, Z15, Z18 . . . ). The unique cutting order identifier for each section can be used to organize the sections into series once the series are defined. The unique cutting order identifier for a section can be contained in the section's serial number.

Returning to FIG. 2A, when the sections are organized into series for different processing, the fiducial elements 101-1, 101-2, 101-3 provide a coordinate system A that allows for a location of features on the sections. In FIG. 2A, the fiducial elements 101-1, 101-2, and 101-3 extend through the entire sample and are rigidly attached to each of the sections.

Figure 2B:
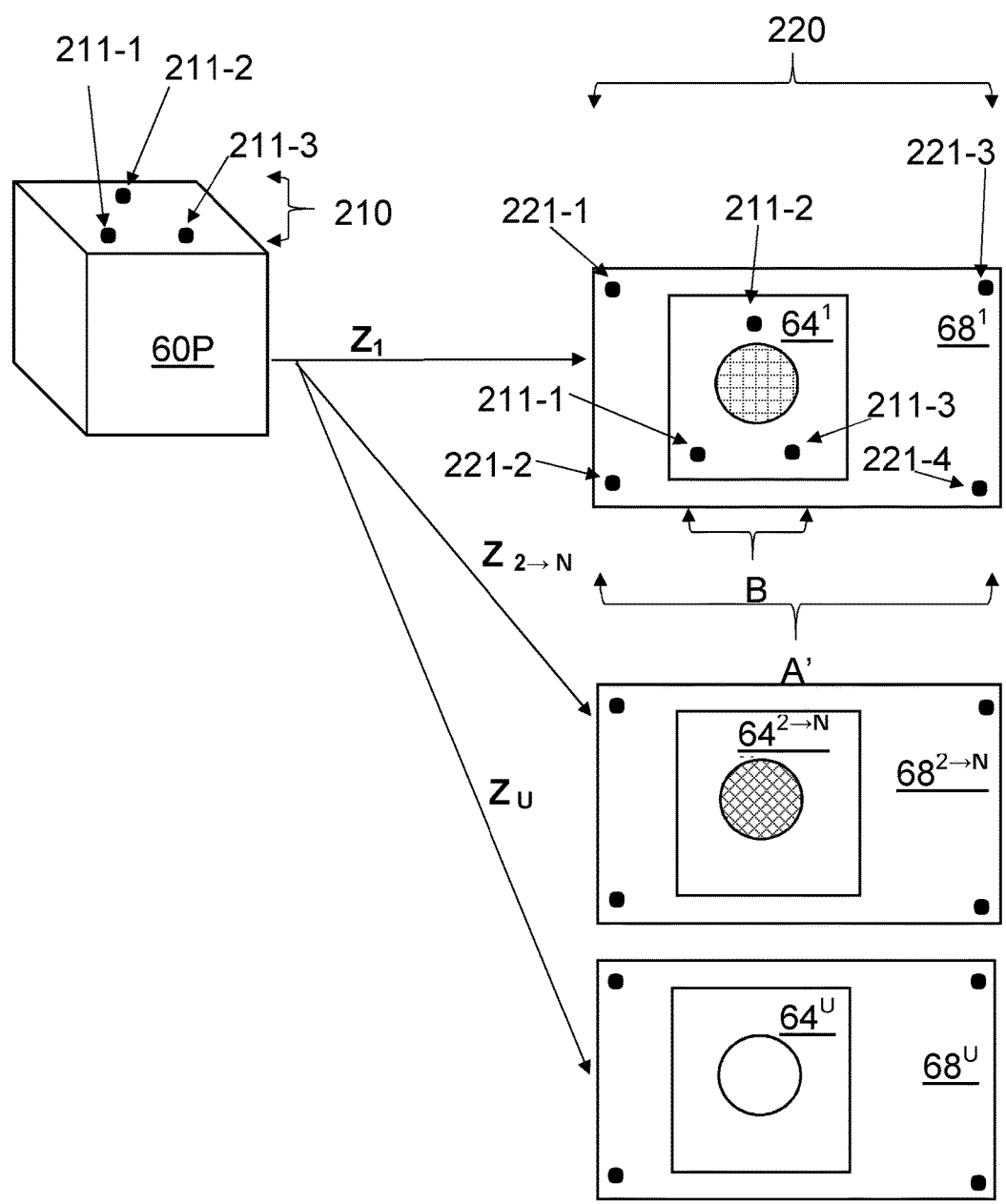
FIG. 2B is a diagrammatic representation of a third embodiment of fiducial elements and the development of a coordinate system for use with identifying positions on sections cut from a block in which fiducial elements are not embedded.

FIG. 2B shows an embodiment of a fiducial element system 210 in which the fiducial elements 211-1, 211-2, 211-3 are applied only to the top surface of the section 60P and do not extend through the length of the sample 60P. When the first section 641 is cut from the sample at position Z1, it contains fiducial elements 211-1, 211-2, 211-3, but any subsequent sections (from positions Z2 on) do not. To compensate for the lack of fiducial elements, the sections (641, 642, 643 . . . ) can be mounted on supports (681, 682, 683 . . . ) such as a slide or a sample tape, and fiducial elements 211-1-211-4, marked thereon. An exemplary sample tape is disclosed in U.S. Patent Application 62/187, 1147, filed Jun. 30, 2015, which has been incorporated by reference.

The coordinate system A' with which the position of features on the sections (641, 642, 643 . . . ) is determined can be developed by mapping the coordinate system B defined by the fiducial elements 211-1, 211-2, 211-3 on section 641 and mounting the sections (641, 642, 643 . . . ) onto the supports (681, 682, 683 . . . ) with great positional accuracy so that the sections are all positioned on their supports exactly the same. The positional accuracy of the mounted sections from support to support renders the coordinate systems A' and B in rigid registry so that coordinate system A' can substitute for coordinate system B. In the subsequent steps, coordinate section A' can be used in subsequent research projects to localize a spatial point on one of the unprocessed sections from series U.

FIG. 3A is a diagrammatic representation of a process for archiving sections on which features have been identified and mapped, and matching features on a test sample with features from the archived sections.

Figure 3B:
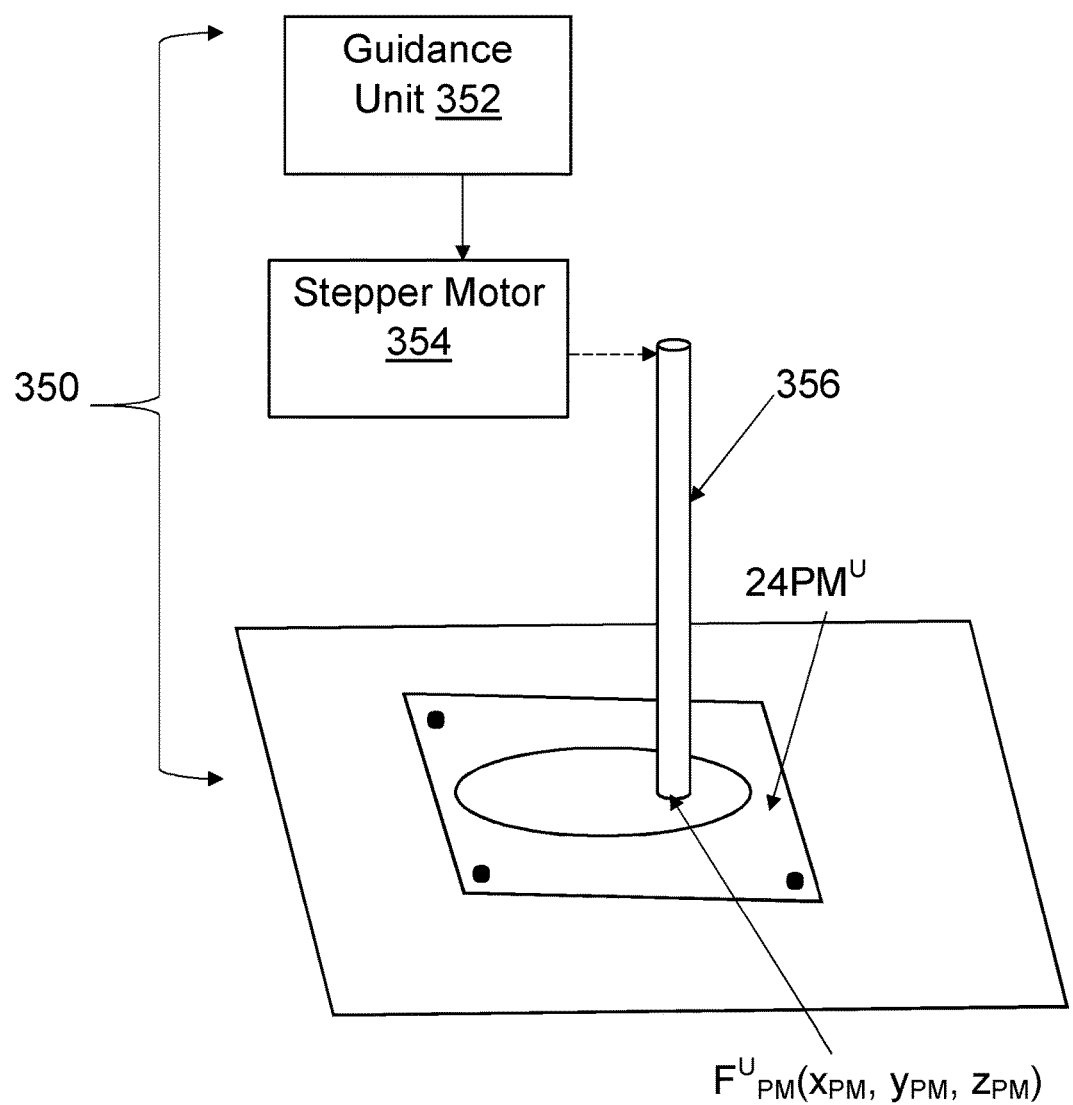
FIG. 3B is a diagrammatic representation of another aspect of the current invention, showing the use to which sections retrieved with the process of FIG. 3A are put.

FIG. 3B is a diagrammatic representation showing the use to which sections retrieved with the process of FIG. 3A are put. A series of histochemical stained sections can be imaged and then subjected to image processing algorithms in order to define features F and feature vectors F(x,y) at each spatial location (x,y) within a section. A z-coordinate can be added to the feature vector based on the unique cutting order identifier associated with the section bearing the feature. Thus the feature vector may take the form Fxy(xa, yb, zc), where:

x identifies the process (such as stain type) to which the section was subjected;
y identifies the feature type,
xa identifies the x-coordinate for the feature on the section 24x;
yb identifies the y coordinate for the feature on the section 24x; and
zc identifies the z coordinate of the section 24x; as determined by its unique cutting order identifier (which can be contained in its serial number).

For section 24I, which is part of Series 1, a z-coordinate z1 can be identified from its serial number, which contains the unique cutting order identifier that indicates its original location along the z-axis of the sample 20P. Since the tape transfer assisted sectioning method is being used, this permits keeping track of the z-coordinate. Thus, the two features F1, F2 of section 24I shown in FIG. 3A, have feature vectors F11(x1, y1, z1), F12(x2, y2, z1).

The processed sections, along with information from the analyses performed on the processed sections, can be stored in the depository 480, which contains section storage 485 for storing the processed sections, and one or more databases to store the information developed from the analyses. In the embodiment disclosed here, the depository 480 may have a features database 488 for storing information about the features identified in the analyses, such as feature types and calculated feature vectors. The depository 480 may also have an image database 486 for storing the images made of the processed sections and related information about the images and imaging processes. Depository 480 also has storage for storing information about the processed and unprocessed sections, such as their serial numbers, including cutting order identifiers, the derived z-coordinate corresponding to serial section number, and the de-identified patient record number, and the coordinate system used to derive the feature vectors.

In subsequent research projects, a user may search the depository 480 to identify sections containing features that could be helpful to their investigations. FIG. 3A shows that a new section of tissue, namely test section 24T from a new patient, can be histochemically processed, using the same or similar histochemical processing as those performed by sections stored in the depository 480. The section 24T is examined for some feature associated with a spatial location (e.g., a specific region contained within a tumor, perhaps containing specific cell types as specified by morphology or histochemical stain). After processing, the section 24T can be imaged and subjected to the same or similar image processing as sections stored in the depository 480, to determine a feature vector FQ(x',y'), where Q denotes query.

Depository 480 can be searched to obtain a best match between the query feature vector FQ(x',y') and a feature vector Fxy(xa, yb, zc) stored in depository 480. The matches are returned as a ranked list based on closeness to the feature vector in question. To query can be designed to return all matches within a set distance of the best match, or return a list of fixed length (e.g., top 10 matches together with the distance scores).

The best match feature vector can be designated FPM $(x_{PM}, y_{PM}, z_{PM})$, where PM corresponds to a specific patient record and $(x_{PM}, y_{PM}, z_{PM})$ is the physical location in the banked tissue that best matches the feature under investigation in the new section 24T. This determines a specific best matched section 24PM, and a specific spatial location FPM $(x_{PM}, y_{PM}, z_{PM})$, on the section 24PM, which potentially matches or contains useful information about the feature under investigation in the new section 24T, or at least provides a starting point for learning more about the feature on section 24T.

Once the best matched section 24PM and feature vector FPM$(x_{PM}, y_{PM}, z_{PM})$ are identified, a series U section 24PMU is identified that is associated with best matched section 24PM. In addition, a best matched feature vector FUPM$(x_{PM}, y_{PM}, z_{PM})$, which is the feature vector on the section 24PMU associated with the best match feature vector FPM$(x_{PM}, y_{PM}, z_{PM})$, is identified. In certain embodiments, the series U section selected to be section 24PMU is the closest in proximity to the best matched section 24PM along the z-axis of the sample from which the sections were cut.

The section 24PMU can be retrieved from the section storage 485, and a small aliquot of tissue can be obtained from the section 24PMU corresponding to the location FUPM$(x_{PM}, y_{PM}, z_{PM})$, $(x_B, y_B)$. In the embodiment shown in FIG. 3B, a tissue extraction unit 350, having a tissue extraction device 356, a guidance unit 352 to detect position according to the coordinate system that was used to originally derive the feature vectors, and a stepper motor 354 to position the tissue extraction device 356. The tissue extraction device 356 can be a tissue punch, which can be used on a piece of tissue attached to a tape, or a pipette, which can be used to extract a small section of tissue.

The tissue extraction device 356 is positioned above the location FUPM$(x_{PM}, y_{PM}, z_{PM})$, $(x_B, y_B)$ using the coordinate system that was used to originally derive the feature vectors. The positioning can be performed manually or automatically using visual guidance from the guidance unit 352 and movement by the stepper motor 35. The tissue extraction device 356 is into physical contact with the location FUPM $(x_{PM}, y_{PM}, z_{PM})$, $(x_B, y_B)$, and a small aliquot of tissue obtained. The small aliquot of tissue thus extracted can be subjected to the desired molecular analysis (eg, DNA or RNA sequencing).

A depository system 400 according to the present invention will now be described in detail with reference to FIGS. 4A-6. The depository system 400 is provided for the purposes of analyzing and storing sections cut from samples, storing information about the sections and the results of the analyses. The depository system 400 is also provided to store unprocessed sections that can be associated with the analyzed sections, and retrieved for future investigations when the analyzed sections with which the unprocessed sections are associated are found to contain features that can be helpful in the future investigations.

Figure 4A:
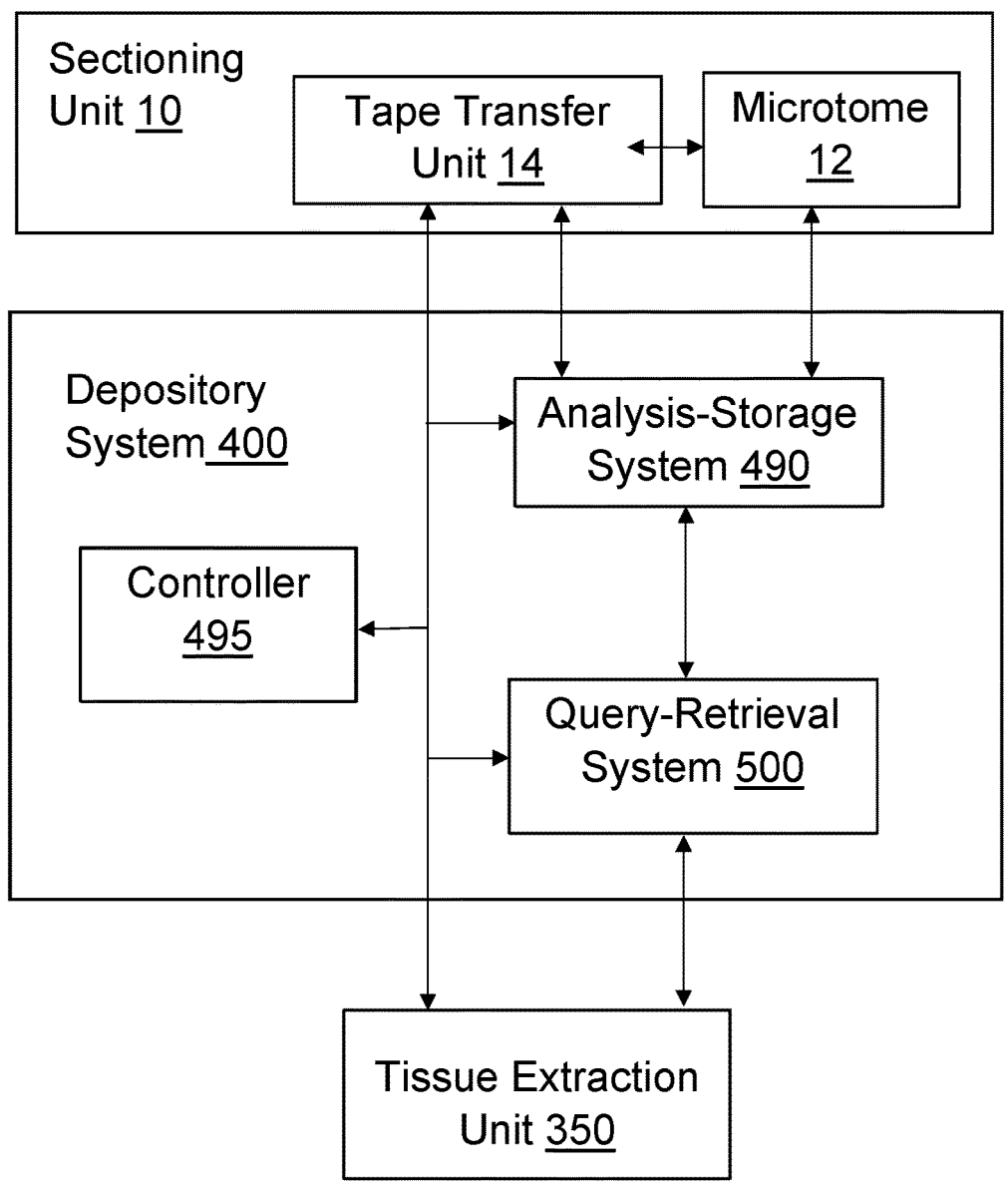
FIG. 4A is a block diagram of an exemplary section handling system with a depository system 480 for use in the process of FIG. 3A.

The depository system 400 has an analysis-storage system 490 that allows a user to identify features of the sample. As noted above, the features could be the spatial distribution of cells of specific morphologies or cells exhibiting identifiable characteristics under specific stains. The depository system 400 also allows for storage of information about the features, the analyzed sections, and unprocessed sections that were cut from the tissue sample in close proximity to the analyzed sections, for use in future studies. As seen in FIG. 4A, the depository system 400 can be electrically and mechanically coupled to a sectioning unit 10 with a microtome 12 and a tape transport system 14 to provide for controlled cutting of sections from samples. A suitable sectioning unit is disclosed at U.S. Patent Application 62/187,114, filed Jun. 30, 2015, which has been incorporated by reference.

The depository system 400 also has a query-retrieval system 500 that allows subsequent users to identify features of a test section, search for a best match among earlier identified features, identify the analyzed section from which the best matched feature was identified, and retrieve an unprocessed section associated with the best matched identified section for use by the users. Optionally, the query-retrieval system 500 can be electrically and mechanically coupled to a tissue extraction unit 350 to facilitate extraction of an aliquot from unprocessed sections that have been retrieved from the depository system 400.

Figure 4B:
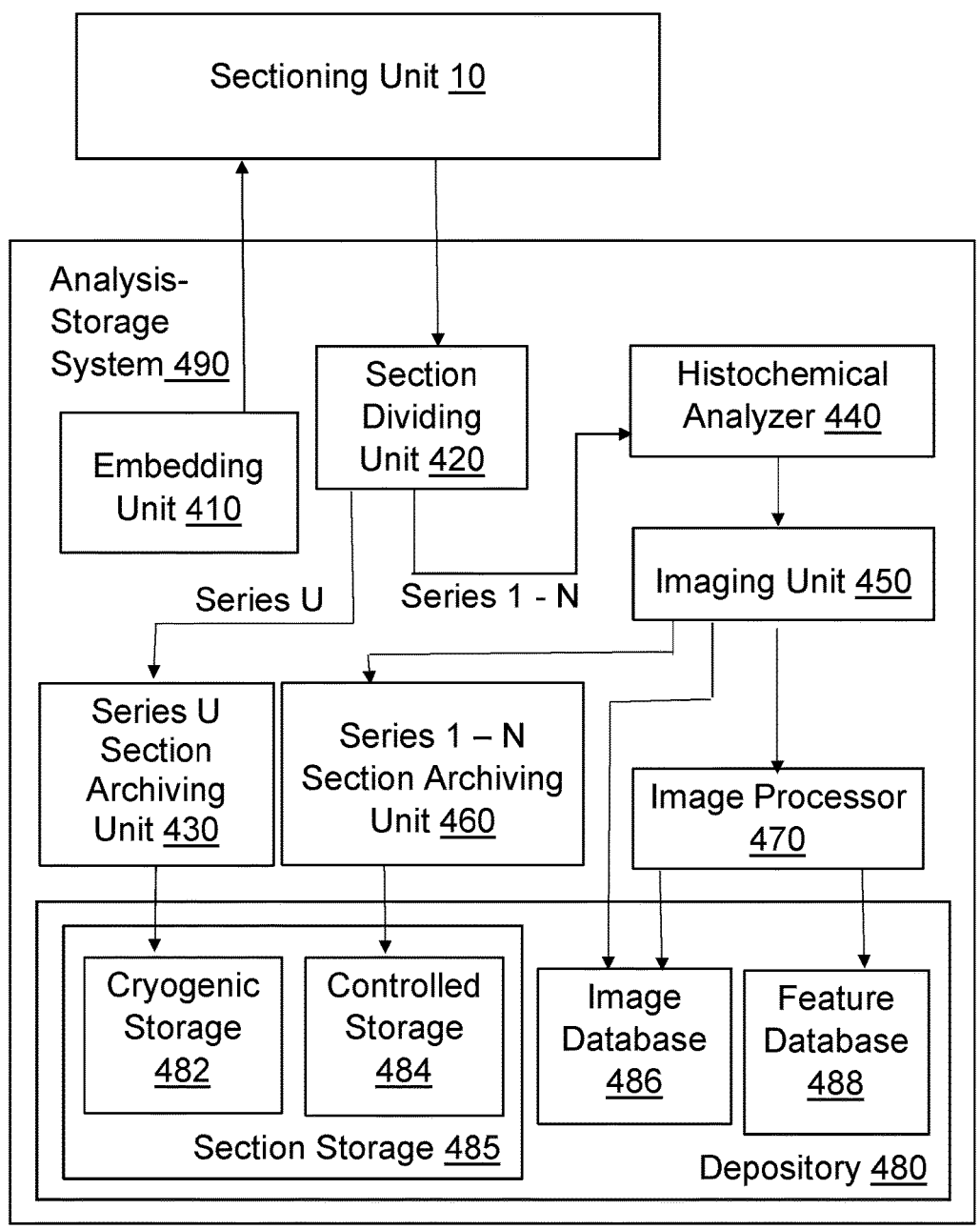
FIG. 4B is a block diagram of one embodiment of the analysis-storage system 490 shown in FIG. 4A.

FIG. 4B is a block diagram of one embodiment of an analysis-storage unit 490 of the depository 400. The analysis-storage system 490 provides analysis of a sample and storage of sections cut therefrom and information about the sections and the analysis. As shown in FIG. 4B, the analysis-storage system 490 has an embedding unit 410 for embedding fiducial elements (such as those shown in FIGS. 1A-1D) into a sample. A sectioning unit 10 has a microtome 12 for cutting the embedded sample into sections and a tape transport unit 14 for transporting the sample from the embedding unit 410 and the cut sections to the section dividing unit 420 in the analysis-storage system 490.

The analysis-storage system 490 has a section dividing unit 420 for maintaining information about the order in which the sections were cut from the sample while dividing the ordered sections into series by the type of processing to which the sections will be subjected. The analysis-storage system 490 also has a Series U section archiving unit 430 for preparing the Series U sections for storage, and a cryogenic storage 482 in a section storage 485 within a depository 480.

For treatment of the sections selected for analysis, the analysis-storage system 490 has a histochemical analyzer 440 for staining the sections, an imaging unit 450 for imaging the stained sections, and an image processor 470 for identifying features of the stained section. In addition, the analysis-storage system 490 also has a Series 1-*n* section archiving unit 460 for preparing the analyzed sections for storage, and a temperature and humidity controlled storage 484 in the section storage 485 for storing the sections that have been subjected to processing and analysis.

Figure 5:
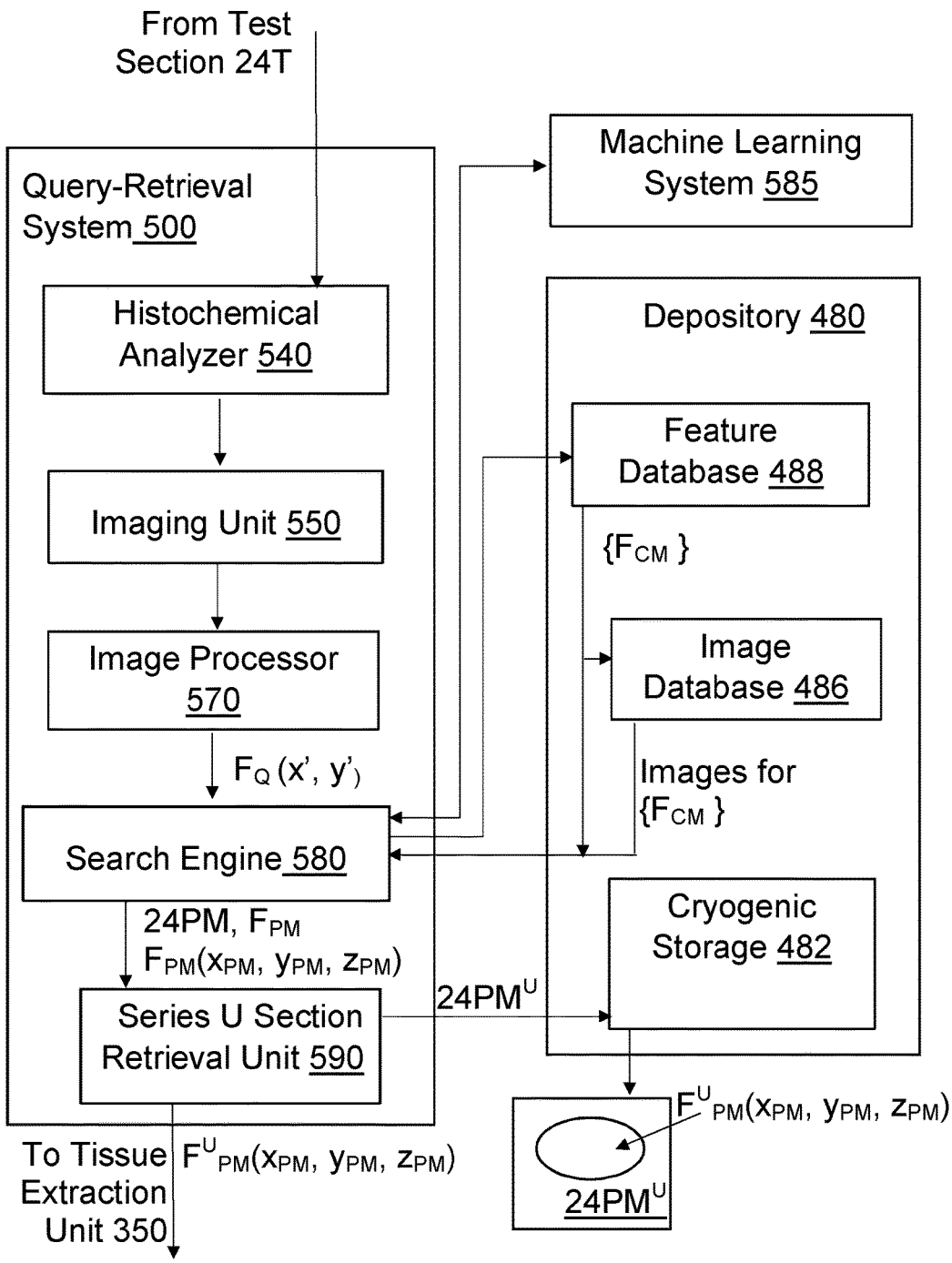
FIG. 5 is a block diagram of one embodiment of the query-retrieval system 500 shown in FIG. 4A.

FIG. 5 is a block diagram of one embodiment of a query-retrieval system 500 of the depository 400. The query-retrieval system 500 provides allows users to identify features of a test section, search for a best match among earlier identified features, identify the analyzed section from which the best matched feature was identified, and retrieve an unprocessed section associated with the best matched identified section for use by the users. As shown in FIG. 5, the query-retrieval system 500 has a histochemical analyzer 540 for staining the test sections, an imaging unit 550 for imaging the stained test sections, and an image processor 570 for identifying one or more features of the stained test sections.

In addition, the query-retrieval system 500 also has a search engine 580 for searching for a best match to the test feature among earlier identified features, and for identifying the analyzed section from which the best matched feature was identified. In certain embodiments, multiple test features can be identified and the search engine 580 may conduct a search of the feature database 488 to identify best matches for each of or a subset of the multiple test features. The query-retrieval system 500 may also have a user interface 520 to allow a researcher to have input into the test feature identification, development of the search query and review of search results.

The search engine 580 can be any suitable type of search engine, including but not limited to a database search engine, a desktop, enterprise or web-based search engine, a centralized or a distributed search engine, and search engine. In certain embodiments, the search engine 580 can be a human-based search engine, in which the researcher or another human filters the search results to clarify their search request and limit the search results The search engine 580 is connected to the user interface 520 so that a researcher may input search parameters and receive search results. The search engine 580 may also have associated with it a machine learning system 585 to allow the search engine 580 to learn from past investigations and past searches and to improve the accuracy of its search results. The query-retrieval system 500 also has a Series U retrieval unit 590 for retrieving an unprocessed section associated with the best matched identified section for use by the users.

In operation, the histochemical analyzer 540, imaging unit 550, and image processor 570 identify a test feature $F_Q(x', y')$ for which similar features from past investigations are sought. The test feature (or subset of features) can be user selected from a list of candidate features via a user interface, or selected automatically by the search engine using the machine learning system 585 and based on the searching algorithms used and how informative this feature (or subset of features) has been in the past. Other suitable selection criteria may be used, such as perceived criticality of the feature to investigation. For simplicity, the following describes the process 500 for finding a best match for a single test feature $F_Q(x', y')$. However, it is to be understood that the process 500 can be used to identify a best match for multiple test features. The search engine 580 conducts a search of the feature database 488 to identify a best match feature $F_{PM}$ that constitutes a best match to $F_Q(x', y')$.

A suitable norm or distance in feature space can be utilized to determine best match. Such a norm could be, for example the Euclidean distance between features vectors, or some other norm such as the p-norm between Feature vectors. The p-norm between two feature vectors (F1,F2, F3, . . . ) and (F1', F2', F3', . . . ) is defined as $[(F1-F1')^p+(F2-F2')^p+(F3-F3')^p+ \ldots ]^{1/p}$, with p=2 giving the Euclidean norm. Components of the feature vector can be suitably weighted to emphasize a particular feature that has proven informative in the past. In other embodiments, the search engine 580 may identify a set $\{F_{CM}\}$ of candidate best match features $F_{PM}$ that could constitute a best match to $F_Q(x', y')$. Returning to the embodiment in which the search engine 580 identifies a set $\{F_{CM}\}$ of candidate best match features for a single test feature, the search engine 580 searches the image database to identify the images associated with the members of the candidate best match features set $\{F_{CM}\}$. In identifying the images, the search engine 580 determines which sections are associated with the candidate best match features.

The search engine 580 determines the best match feature FPM, the feature vector $FPM(x_{PM}, y_{PM}, z_{PM})$ that points to the best match feature FPM, and the section 24PM carrying the best match feature FPM and to which best matched vector $FPM(x_{PM}, y_{PM}, z_{PM})$ points. The search engine may employ artificial intelligence, neural nets, fuzzy logic, and advanced natural language technology to make its determinations. In addition, since the search engine is relatively independent of the other systems and units described herein, it may use with virtually any knowledge providing system, such as, for example, a case-based reasoning system, to aid in its determination. Retrieval of the spatial index can be performed using computed metadata (e.g., density of specific types of cells in space), or by doing content-based image retrieval (i.e., pattern matching to a query image of interest).

The search engine may access the databases of the depository 480 to obtain information, such as information about the sample, section, the processes and procedures underwent by the sections, the types of features, the patient, including non-identifying information about the patient from stored medical records. Further, the search engine may output to the user a set of likely best match features FPM, best match feature vectors FPM($x_{PM}, y_{PM}, z_{PM}$), and their associated sections 24PM, along with a listing of the extent of match, likelihood of applicability, or other ranking for user selection of the most suitable best match. It is to be understood that no two sections from a single sample will be precisely the same, as they are cut from different depths (i.e., different z values) in the tissue. However, features in a sample could be present in more than one section, especially if the sections are cut from depths that are close to each other (i.e., geometrically close z values) in the tissue. Therefore, multiple sections could constitute potential best matches for a test feature. In certain embodiments, the candidate best match features can be returned by the search engine 580 as a ranked list (based on closeness to the feature vector in question or based on the extent of similarity of the candidate best match feature to the test feature). Alternatively, the number of candidate best match feature in a set can be limited by criteria such as returning all matches within a set distance (measured by a set distance of the best match, or return a list of fixed length (e.g. top 10 matches together) with the scores representative of the distance scores, or by scores that represent the extent of similarity of the candidate best match feature to the test feature. One way to identify a best match feature from among multiple candidate best match features is to set a threshold value for the match, so that only matches meeting the threshold (such as an extent of similarity of the candidate best match feature to the test feature) are selected. Another way would be to select one best match using one or more metrics that a best match feature would be required to meet.

However the best match is ultimately determined, the search engine 580 outputs the best match feature FPM, the feature vector FPM($x_{PM}, y_{PM}, z_{PM}$), and the section 24PM to the Series U section retrieval unit 590, which identifies the unprocessed section 24PMU that is most closely associated with the section 24PM. In certain embodiments, the section 24PMU is the one that is closest in proximity to the best matched section 24PM along the z-axis of the sample from which the sections were cut. If the unprocessed section that is most closely associated to be the unprocessed section 24PMU is unavailable (being damaged, being missing, having already been retrieved in an earlier investigation, or for any other reason), then the unprocessed section proximate to the unavailable unprocessed section can be selected as the unprocessed section 24PMU.

The Series U section retrieval unit 590 outputs the identity of the section 24PMU to the cryogenic storage 482 to retrieve the selected section 24PMU. The Series U section retrieval unit 590 also derives the best match feature vector FUPM($x_{PM}, y_{PM}, z_{PM}$) to identify the position on the section 24PMU where the best match feature is likely to be found, based on the feature vector FPM($x_{PM}, y_{PM}, z_{PM}$) of the best match feature FPM and the close association between best match section 24PM and the section 24PMU. The Series U section retrieval unit 590 outputs the best match feature vector FUPM($x_{PM}, y_{PM}, z_{PM}$) to the tissue extraction unit 350 to facilitate extraction of an aliquot from the section 24PMU at the location pointed to by the best match feature vector FUPM($x_{PM}, y_{PM}, z_{PM}$).

Figure 6:
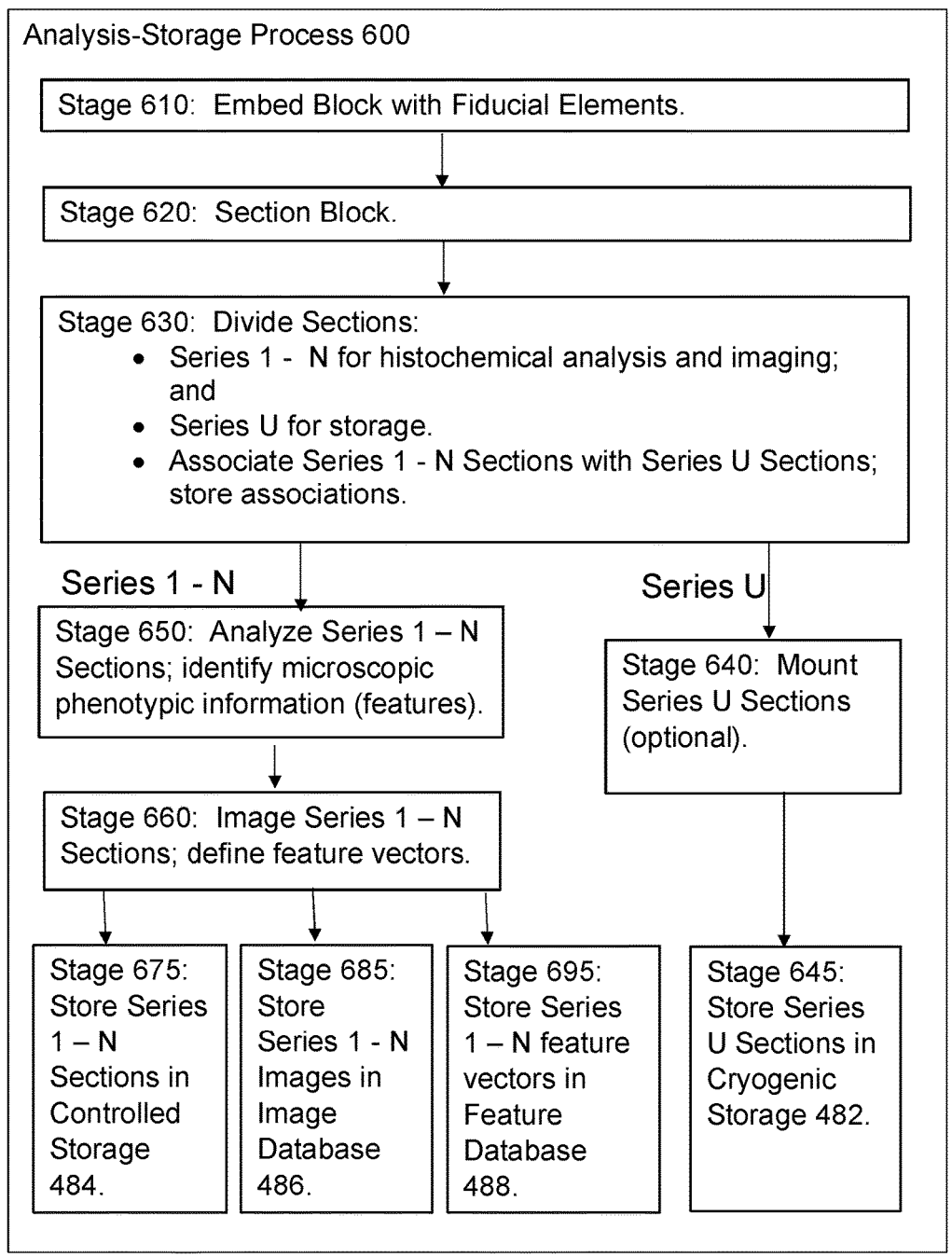
FIG. 6 is a flow chart for one embodiment of an analysis-storage process 600.

FIG. 6 illustrates an exemplary process 600 for analyzing and storing sections. In one embodiment, a sample block is embedded with fiducial elements to provide a coordinate to facilitate analysis across sections in current and future investigation. In a stage 610, the block can be cut into sections, with the order in which the sections are cut being recorded in a unique cutting order identifier. In a stage 630, sections are divided into series, with one or more series targeted for histochemical analysis and imaging; and one series targeted for no or minimal processing and storage. The sections selected for no or minimal processing based on the order in which they were cut from the sample so that, were the sections to be organized into the order in which they were cut from the sample, unprocessed sections would be interleaved with the sections to be processed. In the Stage 630, associations are developed between the sections targeted for processing and those selected for Series U sections; store associations. In certain embodiments, an association between a Series U section and a section to be processed involves an identification of the proximity between the two sections along the z-axis of the sample from which the sections were cut. In an optional stage 640, the Series U sections are mounted on a substrate for support in preparation for storing in a cryogenic storage in a stage 645.

In a stage 650, the sections targeted for processing are analyzed to identify microscopic phenotypic information (features). In a stage 660, they are imaged and 3-D locational feature vectors are derived to identify the location of features identified during the analysis. The z-axis is determined by reference to the location of the section in the sample before it was cut. In a stage 675, the sections are stored in a controlled storage environment, while in a stage 685, their associated images are stored in an image database, and in a stage 695, the features vectors are stored in a feature database.

Figure 7:
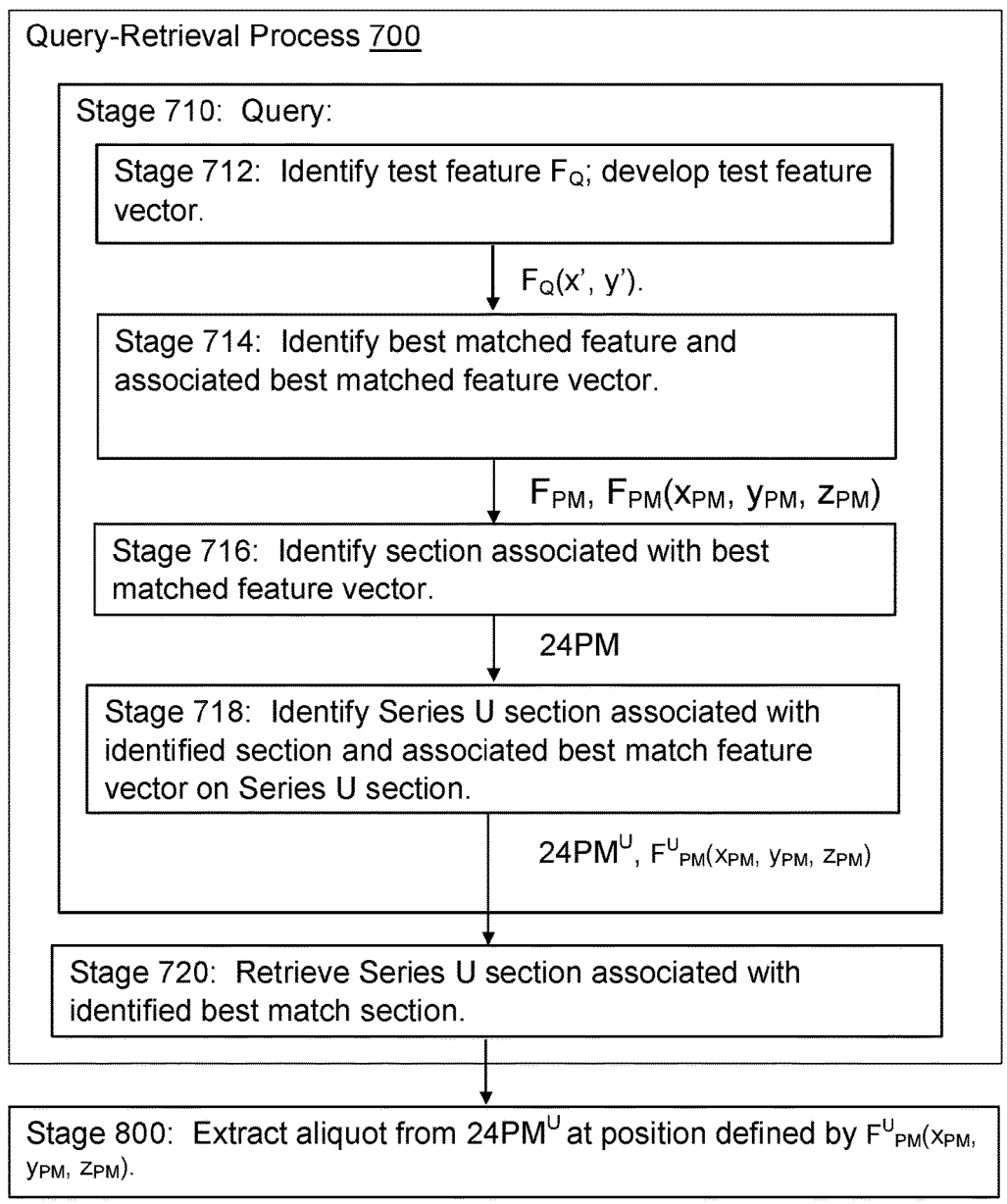
FIG. 7 is a flow chart for one embodiment of a query-retrieval process 700.

FIG. 7 illustrates an exemplary process 700 for querying the depository 480 to identify previously processed sections having test features that can be relevant in current research and retrieving unprocessed sections stored in the depository 480 that are closely associated with the previously processed sections. The progress 700 has a query process 710 process with a stage 712 for identifying a query feature FQ from a test section and developing a query feature vector to pinpoint a location of the query vector on the test section.

The process 700 has a stage 714 for identifying a best matched feature (a feature that best matches the query vector) and a best matched feature vector that is associated with the best matched feature. In a stage 716: the section associated with the best matched feature vector I identified, and, in a stage 178, the unprocessed section that had been stored for subsequent use and that is the most closely associated with the best match section and its associated best match feature vector is identified.

The process 700 also has a stage 720 for retrieving the unprocessed section that is associated with the most closely associated with the best match section and its associated best match feature vector is identified.

In a stage 800, a small aliquot of the identified unprocessed section is extracted at a position at the location pointed to by the best match feature vector FUPM($x_{PM}, y_{PM}, z_{PM}$).

EXAMPLES

As an illustrative example of the use of the systems and processes described in this patent, it can be desirable to retrieve portions of tissue sections from biopsies performed on a group of patients with a particular cancer, for example a lung cancer or a breast cancer, with a specific microscopic phenotype, e.g., an increased number of cells with a given morphological characteristic visible in histological imaging. The retrieved portions of tissue can be subjected to molecular analyses in order to identify mutated genomic sequences, abnormal RNA transcripts or protein expression. Such analysis may reveal a common genotype or molecular phenotype corresponding to the microscopic phenotype in question, thus leading to better understanding of the pathology, and also permitting targeted therapy or patient selection in a clinical trial.

Such a study could start with creating a series of sections as disclosed above from a biopsy in a patient. An anatomic pathologist may identify a local region in one or more histological images, with a stain corresponding to one of the histochemical or immunochemical stains employed by the CBIR-assisted biobank disclosed herein. The anatomic pathologist may visually examine the images in question from the patient's biopsy, and demarcate a small portion of the tissue section showing an abnormal microscopic phenotype (in the judgment of the pathologist), such as the excess in number of cells of a specific type. This histological image may constitute a "query" image, input it to the CBIR-assisted biobank system, along with a demarcation of the small region inside the image showing the abnormal microscopic phenotype.

The query mechanism may exploit information present in the query image at multiple length scales. Part of the weight in the query may be given to the tissue type encompassing the image, and this information is present throughout the query image and provides context; similarly, part of the weight will be given to the specific region demarcated within the query image. In preparing the query, image-processing steps may be taken to (i) segment out biologically meaningful objects such as individual cell bodies and/or nuclei present in those cell bodies; (ii) classifying those objects, i.e., cell bodies or nuclei, into types; (iii) determining the densities of the corresponding objects of a given type; and (iv) determining the shapes and sizes of regions in which the objects of specified type are located, from which densities of the objects may be determined. The rationale for such a procedure is that pathological tissues may contain objects of abnormal types, or abnormal numbers or densities of such objects, or abnormal geometrical distributions of such objects.

Thus, pre-processing of the image may be performed to extract features capturing a variety of biologically and histopathologically meaningful information, and the anatomic pathologist may interactively choose between the relative weights of such features, in developing the query. It is also possible that the pathologist directly demarcates individual objects in the image for which the densities are of interest. In this manner the anatomic pathologist may fine-tune the query beyond selecting an image and demarcating a region of the image, thus improving the precision of the query based search. The features selected directly or indirectly by the anatomic pathologist are used to formulate the query. In performing the query, the absolute values of these features may be used (such as the densities), in addition the relative values of the features compared with a normative or typical tissue pool may be used also to refine the query.

The search inquiry can be developed using any conventional process using any conventional search engine. As noted above, the test feature (or subset of features) can be user selected from a list of candidate features via a user interface, or selected automatically by the search engine using the machine learning system 585 and based on the searching algorithms used and extent of usefulness this feature (or subset of features) has been in the past. Other suitable selection criteria may be used, such as perceived criticality of the feature to investigation.

Once the region is demarcated the researcher may input just the image and a demarcation of a region of the image, and allow the search engine to construct the query from the demarcation alone, figuring out why it was demarcated, such as identifying the characteristic (e.g., an excess of a particular type of cells in the region) based on the region demarcation. The demarcation of the region itself can be a characteristic (location of the region relative to other nearby regions). The image processor can be used to count the typed cells, then develop a density of the identified cells, compare the density to a threshold density, and, if it exceeds the density, look for sections having regions with identified cells of a specified type or density. Alternatively, the search engine and image processor may look for sections having abnormal clusters of the identified cells.

The researcher may input, via the user interface 520, more information than just the image and a demarcation of a region of the image. For example, the researcher may input information such as why the region was demarcated (in this case, an excess of a particular type of cells in the region). The researcher may input the type of cell, counts of the number of cells in the demarcated region, the cell density in the region. The researcher may indicate what is important to the query—size of region, number of cells, size of cells, type of cells, density, etc.

The system may then proceed in the manner disclosed herein to retrieve a section, and therefore small regions within the section, that provided the best match to the demarcated abnormal region in the query image. As a special case, the demarcated region could be the entire section, in which case a match will be retrieved for the entire query image. In a further embodiment, at the direction of the user, multiple sections that constitute best matches can be retrieved. As an example, the top 100 such matches can be retrieved. In a further embodiment, the search engine 580 can be configured to limit the multiple best match sections to each being associated with different patients or to limit the multiple best match sections to each associated with a different patient sample or section included in the biobank.

Alternatively, the search engine 580 can be configured to allow some or all of the multiple best matched sections to each being associated with the same patient. The search engine 580 may also be configured to allow only a certain number of best match sections that may originate from the same patient. In still further embodiments, the search engine 580 can be configured to allow some or all of the multiple best matches sections allow a user to select, via the user interface 520, the above-disclosed parameters.

Once the best match sections are identified and retrieved in accordance with the processes and systems disclosed herein, aliquots of tissue can be extracted from the identified sections as disclosed herein, and these can be subjected to genomic, transcriptomic or proteomic analysis in order to identify common changes occurring in the abnormal regions on the test section and the best match section(s).

In another embodiment, when the anatomic pathologist visually examines the images in question from the patient's biopsy and demarcates a small portion of the tissue section showing an abnormal microscopic phenotype, the pathologist may also demarcate a non-pathological or normal portion of the section, to serve as a baseline or comparison. The system may then proceed in the manner disclosed herein to retrieve the section or sections containing the small regions within those sections that best match the demarcated abnormal region. In so doing, the system also retrieves the corresponding "normal" region(s) from the best matched section(s). In further embodiments, "normal" regions can be retrieved from a different section. Selection of a different section for establishing a "normal" region baseline may be due to two reasons. First such a procedure can increase the amount of baseline image material and this can improve the classification between pathological and normal tissues by better learning the structure of the normal tissues, a methodology that is known as semi-supervised learning. Second, there may not be enough "normal" or baseline region in the section containing the pathological tissue. The pathologist can select both normal regions with a section, or designate a whole section as "normal".

The system may then proceed in the manner disclosed herein to extract aliquots of tissue from the identified "abnormal" as well as "normal" regions of the identified "best match" sections. The best match can be determined by choosing the closest feature vector corresponding to the region of interest. A variety of metrics may be used in the space of feature vectors, such as the Euclidean metric, weighted Euclidean metric, or a p-norm, as will be clear to those skilled in the art of statistical analysis. The aliquots of tissue extracted can be used, during genomic, transcriptomic or proteomic analysis, to identify common changes occurring in the abnormal regions (as compared to the normal regions). By being able to choose small portions of sections, with matching microscopic phenotypes, the researcher or physician performing the study may obtain specific genomic, transcriptomic or proteomic signatures characteristic of the cancer in question, with high accuracy. The accuracy of the signature would be high because this method chooses a small aliquot of tissue (thus removing confounds due to heterogeneity), and also obtains a matched small aliquot of a normal tissue sample. This kind of study would be uniquely assisted by the CBIR-assisted biobank disclosed herein.

Further, such a procedure may aid a clinical trial by identifying previous cases in which a specific microscopic phenotype is present in local regions of a cancer biopsy. This could aid patient selection in a clinical trial. For a candidate patient, a biopsy would be performed, and the anatomic pathologist would demarcate abnormal and normal regions within stained histological images from this biopsy. Following this, closest matching sections with corresponding microscopic phenotypes would be identified from the biobank, and aliquots of tissue extracted, as well as the de-identified patient records obtained from the matching samples. A criterion for allowing a new patient to be admitted to the study in question can be a predetermined level of similarity between specified clinical characteristics of the new patient and those of the previous best-matched patients in terms of molecular phenotype, diagnostics, therapy and outcome.

It can be seen that the embodiments of the systems and methods disclosed here can be used to greatly facilitate phenotypic selection of a tissue sample. It will allow for efficient identification of similar features and patterns from earlier investigations, and will thus aid in improving research results. Results will be obtained that are more accurate than available from patient medical record only, or only from a histochemical stain on a nearby section but without the ability to precisely spatially localize the tissue micro-region of interest. When this invention is combined with other inventions that mechanize tasks such as use of a microtome itself and subsequent sample manipulation, the entire process can be automated and placed under computer control.

Thus, presence of a spatial index (constituted by the series of images of histologically stained sections, together with processed data for those sections), will permit accurate and precise retrieval of a location of interest—not present in current biobanking methods (where the entire block or blank section is retrieved). The lack of spatial distortion due to tape transfer and application of an x-y-z coordinate system will permit precise retrieval of an image location, thus saving tissue samples (e.g., only one small element of a biobanked section may then be retrieved for further analysis).

As shown in FIG. 4A, the depository system 400 has a processor 495 electrically coupled to the units and systems disclosed herein for controlling the operation of the units and systems. These steps disclosed above can be operator controlled using the processor 495 inside the depository system 400 (as shown in FIG. 4A), or by a controller (not shown) outside the system, that communicates electrically or mechanically with the herein described mechanisms.

The components depicted in the Figures can be operatively connected to one another via a network, such as the Internet or an intranet, or via any type of wired or wireless communication system. Connections can be implemented through a direct communication link, a local area network (LAN), a wide area network (WAN) and/or other suitable connections.

One or more of the components depicted in the Figures can be implemented in software on one or more computing systems. For example, they may comprise one or more applications, which may comprise one or more computer-readable instructions which, when executed by a processor, cause a computer to perform steps of a method, or they can be combined to provide multiple functionalities. Further, while the units and systems are shown in the Figures as associated with a specific processor, such as systems 490, 500 and the processor 495, it is to be understood that the units and systems may operate on any other processor shown or not shown.

Further, the instructions for the units and systems can be stored on the storage device associated with the specific processor or any other storage device, or they can be stored on one or more storage devices, and transferred to run on the shown processor or other or multiple processors. Computer-readable instructions can be stored on a computer-readable medium, such as a memory or disk. Such media typically provide non-transitory storage. Alternatively, one or more of the components depicted in FIG. 1 can be hardware components or combinations of hardware and software such as, for example, special purpose computers or general purpose computers. A computer or computer system may also comprise an internal or external database. The components of a computer or computer system may connect through a local bus interface.

One skilled in the art will appreciate that although only one or two of the components identified above is depicted in the Figures, any number of any of these components can be provided. For example, while only one controller 495 is shown in FIG. 4A, it is to be understood that multiple controllers could be employed instead. Furthermore, one of ordinary skill in the art will recognize that there can be more than one search engine 580, or more than one image processor 470.

The databases and storage units shown in FIG. 4B can be implemented as separate databases and repositories as shown in FIG. 4B or as one or more internal databases stored, for example, on the processor 495 in FIG. 4A. Units of the depository 480, the image processor 470, and the search engine 580 can be accessed by other components in system 400 directly via an external connection or via a network (not shown).

What is claimed is:

1. A method of preparing a series of sections of a specimen, said method comprising:
    a) mounting a specimen block on a microtome so as to expose said specimen blockface;
    b) establishing a two dimensional coordinate system co-planar to each of said sections to allow for spatial localization of features identified on said sections, wherein said two dimensional coordinate system is established by adding one or more fiducial element to said specimen block outside of said specimen;
    c) establishing a third coordinate system z perpendicular to said blockface, said coordinate system comprising a set of ordered, iterative, sequential sections of said specimen, said series prepared by:
        i) adhering a support tape to said specimen blockface;
        ii) cutting a thin section from said specimen co-planar with said blockface, and removing from said blockface said thin section attached to said support tape thereby producing a tape-mounted section having two dimensional (x,y) coordinates;
        iii) repeating steps (i) and (ii) for at least z times; and
        iv) with each repetition of (i) and (ii) above, retaining said tape-mounted sections in sequential order of z=1→z=n to preserve a series of tape-mounted sections, wherein said two dimensional coordinates (x,y) of a section z=n are in alignment with said two dimensional coordinates (x,y) of a section z=n+1.

2. The method of claim 1, wherein said specimen block comprises an embedding material, and said one or more fiducial element is added to said embedding medium outside of said specimen.

3. A method of preparing a series of sections of a specimen, said method comprising:
    a) mounting a specimen block on a microtome so as to expose said specimen blockface;
    b) establishing a two dimensional coordinate system co-planar to each of said sections to allow for spatial localization of features identified on said sections;
    c) establishing a third coordinate system z perpendicular to said blockface, said coordinate system comprising a set of ordered, iterative, sequential sections of said specimen, said series prepared by:
        i) adhering a support tape to said specimen blockface, wherein said support is labelled with a set of coordinate points to establish said two dimensional (x,y) coordinate system co-planar with said blockface;
        ii) cutting a thin section from said specimen co-planar with said blockface, and removing from said blockface said thin section attached to said support tape thereby producing a tape-mounted section having two dimensional (x,y) coordinates;
        iii) repeating steps (i) and (ii) for at least z times; and
        iv) with each repetition of (i) and (ii) above, retaining said tape-mounted sections in sequential order of z=1→z=n to preserve a series of tape-mounted sections, wherein said two dimensional coordinates (x,y) of a section z=n are in alignment with said two dimensional coordinates (x,y) of a section z=n+1;
    d) further comprising establishing said two dimensional coordinate system on an outer facing surface of said specimen block by adding one or more fiducial element solely to said facing surface.

4. A method of preparing a series of sections of a specimen, said method comprising:
    a) mounting a specimen block on a microtome so as to expose said specimen blockface;
    b) establishing a two dimensional coordinate system co-planar to each of said sections to allow for spatial localization of features identified on said sections, wherein said specimen is equipped with at least two fiducial elements to establish said two dimensional (x,y) coordinate system co-planar with said blockface;
    c) establishing a third coordinate system z perpendicular to said blockface, said coordinate system comprising a set of ordered, iterative, sequential sections of said specimen, said series prepared by:
        i) adhering a support tape to said specimen blockface;
        ii) cutting a thin section from said specimen co-planar with said blockface, and removing from said blockface said thin section attached to said support tape thereby producing a tape-mounted section having two dimensional (x,y) coordinates;
        iii) repeating steps (i) and (ii) for at least z times; and
        iv) with each repetition of (i) and (ii) above, retaining said tape-mounted sections in sequential order of z=1→z=n to preserve a series of tape-mounted sections.

5. The method of claim 4, wherein said support is labelled with a set of coordinate points to establish said two dimensional (x,y) coordinate system co-planar with said blockface.

6. The method of claim 5, wherein said support is labelled with the value n of said third coordinate system z.

7. The method of claim 4, wherein said adhering comprises a chemical adhesive.

8. The method of claim 4, wherein said specimen is equipped with at least three fiducial elements to establish said two dimensional (x,y) coordinate system co-planar with said blockface.

9. A method of preparing a series of sections of a specimen, said method comprising:
    a) mounting a specimen block on a microtome so as to expose said specimen blockface;
    b) establishing a two dimensional coordinate system co-planar to each of said sections to allow for spatial localization of features identified on said sections;
    c) establishing a third coordinate system z perpendicular to said blockface, said coordinate system comprising a set of ordered, iterative, sequential sections of said specimen, said series prepared by:
        i) adhering a support tape to said specimen blockface, wherein said adhering comprises a static property;
        ii) cutting a thin section from said specimen co-planar with said blockface, and removing from said blockface said thin section attached to said support tape thereby producing a tape-mounted section having two dimensional (x,y) coordinates;
        iii) repeating steps (i) and (ii) for at least z times; and
        iv) with each repetition of (i) and (ii) above, retaining said tape-mounted sections in sequential order of z=1→z=n to preserve a series of tape-mounted sections.

10. A method of preparing a series of sections of a specimen, said method comprising:
    a) mounting a specimen block on a microtome so as to expose said specimen blockface;

b) establishing a two dimensional coordinate system co-planar to each of said sections to allow for spatial localization of features identified on said sections;

c) establishing a third coordinate system z perpendicular to said blockface, said coordinate system comprising a set of ordered, iterative, sequential sections of said specimen, said series prepared by:

i) adhering a support tape to said specimen blockface;

ii) cutting a thin section from said specimen co-planar with said blockface, and removing from said blockface said thin section attached to said support tape thereby producing a tape-mounted section having two dimensional (x,y) coordinates;

iii) repeating steps (i) and (ii) for at least z times; and iv) with each repetition of (i) and (ii) above, retaining said tape-mounted sections in sequential order of z=1→z=n to preserve a series of tape-mounted sections;

d) dividing said series of sections into at least two sub-series; and e) designating a first sub-series of said two sub-series to be processed for identification of features of said specimen, while designating a second sub-series of said two sub-series to remain unprocessed.

11. The method of claim 10, wherein processing said sub-series to identify features of said specimen comprises treating each section of said sub-series histologically.

12. The method of claim 10, further comprising analyzing each section of said sub-series to reveal microscopic phenotypic information and cellular features.

* * * * *